(12) United States Patent
Yokono

(10) Patent No.: US 7,152,472 B2
(45) Date of Patent: Dec. 26, 2006

(54) MEASURING APPARATUS, MEASURING METHOD AND COMPUTER PROGRAM PRODUCT THEREFOR

(75) Inventor: Masahiro Yokono, Yokkaichi (JP)

(73) Assignee: Sumitomo Wiring Systems, Ltd. (JP)

( * ) Notice: Subject to any disclaimer, the term of this patent is extended or adjusted under 35 U.S.C. 154(b) by 181 days.

(21) Appl. No.: 10/973,641

(22) Filed: Oct. 26, 2004

(65) Prior Publication Data

US 2005/0087022 A1    Apr. 28, 2005

(30) Foreign Application Priority Data

Oct. 27, 2003 (JP) .............................. 2003-366108
Feb. 23, 2004 (JP) .............................. 2004-046844

(51) Int. Cl.
*B23Q 17/00* (2006.01)

(52) U.S. Cl. ...................................... 73/432.1

(58) Field of Classification Search ...................... None
See application file for complete search history.

(56) References Cited

U.S. PATENT DOCUMENTS

| 4,867,710 A | 9/1989 | Harting et al. |
| 5,855,138 A | 1/1999 | Curry et al. |
| 6,085,604 A * | 7/2000 | Koubuchi et al. ......... 73/865.8 |
| 2003/0079338 A1* | 5/2003 | Juranitch et al. ............. 29/705 |
| 2003/0236009 A1 | 12/2003 | Tsuchiya |
| 2005/0037644 A1* | 2/2005 | Ravert et al. ................. 439/82 |

FOREIGN PATENT DOCUMENTS

JP         3-23330         1/1991

* cited by examiner

*Primary Examiner*—Robert Raevis
(74) *Attorney, Agent, or Firm*—Gerald E. Hespos; Anthony J. Casella

(57) ABSTRACT

A press-in portion (11) of a press-fit terminal (10) is held by jigs (21) from opposite sides along a direction substantially normal to the longitudinal direction of the press-in portion (11), and a load (F) acting on the movable jig (21b) and a displacement amount of the movable jig (21b) are measured at this time and the measurement data are written in a data table for terminal. Then, a load (Fp) at a point of coincidence of the data table for circuit board written with the load (F) necessary to widen a hole (H) of a circuit board (K) and a hole diameter of the widened hole (H) and a data table for terminal obtained by the measurement is obtained. Whether the load (Fp) at the point of coincidence lies within a judgment reference range is judged and this judgment result is displayed on a display (44).

25 Claims, 31 Drawing Sheets

FIG. 9

|  | HOLE DIAMETER d | LOAD F |
|---|---|---|
| 1 | ... | ... |
| 2 | ... | ... |
| 3 | ... | ... |
| ... | ... | ... |
| n | ... | ... |

FIG. 22

| JIG | TARGET VALUE OF HOLE DIAMETER | MEASURING METHOD | JUDGING METHOD |
|---|---|---|---|
| JIG A | STARTD VALUE $d_0$ | DES. DISPLACEMENT/ DES. LOAD MEASUREMENT | DRAG/ DEFORMATION JUDGMENT |
| JIG B | MAX. VALUE $d_{max}$ | POINT OF COINCEDENCE MEASUREMENT | RESILIENTLY RESTORED AMOUNT JUDGMENT |
| JIG C | MINI. VALUE $d_{min}$ | ROUND TRIP MEASUREMENT | DRAG/ DEFORMATION JUDGMENT + RESILIENTLY RESTORED AMOUNT JUDGMENT |
| JIG D | MAX./MINI VALUE | --- | NO JUDGMENT |
| --- | STANDARD/MAX./ MINI VALUE | --- | --- |

JUDGMENT (RESILIENTLY RESTORED AMOUNT JUDGMENT)

MEASURING APPARATUS, MEASURING METHOD AND COMPUTER PROGRAM PRODUCT THEREFOR

BACKGROUND OF THE INVENTION

1. Field of the Invention

The invention relates to a measuring or detecting apparatus, to a measuring or detecting method and to a computer program product therefor.

2. Description of the Related Art

Japanese Unexamined Utility Model Publication No. H03-23330 discloses an apparatus for measuring a holding force of a press-fit terminal in a hole of the circuit board. The apparatus measures the holding force by actually mounting a press-in portion into a circuit board for testing. Thus, both the terminal fitting and the circuit board must be replaced every time a measurement is made, and costs are high. Further, the deformations of the respective press-in portions are not necessarily always constant. Accordingly, measurement values are likely to vary, and it has been difficult to obtain highly precise measurement values.

The invention was developed in view of the above problems, and an object thereof is to provide a measuring apparatus and method which can provide highly precise measurement or detection values at low costs.

SUMMARY OF THE INVENTION

The invention relates to a measuring or detecting apparatus designed to obtain a retaining force that acts when a press-in portion of a press-fit terminal is pressed into a hole of an electric/electronic device, such as a circuit board. The press-in portion is squeezed and substantially widens the hole. The apparatus comprises at least one pair of jigs that are displaceable to hold the press-in portion from substantially opposite sides along a direction at an angle, and preferably substantially normal to the longitudinal direction of the press-in portion. The jigs are capable of forming a substitution hole having a dimension substantially corresponding to a diameter of the hole when a target position is reached. The apparatus also includes a displacement amount measuring means for measuring a displacement amount of the jigs. A load measuring means measures a load acting on the jigs from the press-in portion when the jigs are moved closer to the press-in portion. A storage stores a data table for electric/electronic device written with or containing a load necessary to widen or modify the hole of the electric/electronic device and the hole diameter of the widened hole. A calculating portion outputs or writes the measured load and the hole diameter between the two jigs obtained from the measured displacement amount of the jigs and calculates a load at a point of coincidence of the data table for terminal and the data table for electric/electronic device.

Here, the drag is a force acting on the hole of the circuit board in a direction normal to vertical direction or longitudinal direction of the press-in portion with the press-in portion pressed in the hole, in other words, a force contributing to preventing the press-in portion from coming out of the hole or retaining it therein.

When the two jigs are relatively displaced toward the target position to form or define the substitution hole, the press-in portion is held or engaged by the two jigs from opposite side along the direction at an angle different from 0° or 180°, preferably substantially normal to the longitudinal direction of the press-in portion. In this process, the load measured by the load measuring means and the hole diameter between the two jigs obtained from the displacement amount of the jigs measured by the displacement amount measuring means are written or outputted in the data table for terminal. The load at the point of coincidence of the data table for terminal and the data table for electric/electronic device (preferably the data table for circuit board) stored in the storage is obtained or retrieved. The load at this time is the one obtained when the squeezed press-in portion and the widened hole have the substantially same size, i.e. corresponds to or is a measure of a drag or retaining force when the press-in portion is held in the hole. This drag is a force acting on the hole of the circuit board in the direction at an angle different from 0° or 180°, preferably substantially normal to vertical direction or the longitudinal direction of the press-in portion, i.e. a force contributing to preventing the press-in portion from coming out of the hole i.e. contributing to the retaining force.

Since the load of the press-in portion is measured by the jigs in this way, it is not necessary to prepare a circuit board for testing unlike a prior art measuring apparatus for measuring a holding force by actually mounting the press-in portion into the circuit board for testing. Thus, costs can be reduced. Further, since the press-in portion is held by a pair of jigs from opposite sides along the direction at an angle different from 0° or 180°, preferably substantially normal to the longitudinal direction of the press-in portion, the deformation of the press-in portion advantageously can be substantially kept constant, with the result that more precise measurement values than those given by the prior art measuring apparatus can be obtained.

According to a preferred embodiment of the invention, there are further provided: a judging means for judging or discriminating whether or not the load at the point of coincidence of the two data tables lies within a judgment reference range saved in the storage to judge whether or not the press-fit terminal is good, and preferably a notifying means for notifying a judgment result by the judging means to an operator.

Since the operator needs not judge whether or not the measured press-fit terminal is good, operability is better.

Preferably, the judging means also judges or discriminates whether or not the measured load is constantly increasing as the hole diameter between the two jigs decreases.

Whether or not the press-in portion is properly deformed can also be judged or discriminated. For example, if the load decreases halfway after an increase, there is a possibility that the press-in portion is undergoing a buckling deformation or the like. Therefore, the press-in portion is judged to be defect.

Further preferably, the notifying means is or comprises a display for displaying the judgment result.

The judgment result can be notified to the operator by means of the display.

Still further preferably, at least one of a terminal characteristic graph generated based on the data table for terminal, a board characteristic graph generated based on the data table for electric/electronic device (preferably the data table for circuit board) and the judgment reference range can be outputted, preferably displayed on the display.

The operator can be let to know developments of the measurement and those of the judgment by displaying the terminal characteristic graph, the board characteristic graph and the judgment reference range in addition to the judgment result.

Most preferably, there are at least two kinds of jigs including large-diameter jigs capable of forming a substitution hole having a dimension corresponding to a maximum value of a tolerance of the hole diameter of the hole when the target position is reached, and/or small-diameter jigs capable of forming a substitution hole having a dimension corresponding to a minimum value of the tolerance of the hole diameter of the hole when the target position is reached, these jigs being exchangeably provided, there are at least two kinds of data tables for electric/electronic device (preferably data table for circuit board) including a large-diameter data table obtained by setting the maximum value as the hole diameter at a starting point, and a small-diameter data table obtained by setting the minimum value as the hole diameter at the starting point, and the calculating portion calculates a load at a point of coincidence of the data table for electric/electronic device (preferably data table for circuit board) conforming to the selected jigs and the data table for the measured terminal.

A precise drag in view of a tolerance range of the hole can be obtained.

According to a further preferred embodiment of the invention, there are further provided: a jig accommodating box provided with accommodating chambers for at least partly accommodating the respective jigs, a jig detecting means provided in correspondence with the respective jigs for detecting whether or not the respective jigs are at least partly accommodated in the accommodating chambers, and a verifying means for verifying whether or not the jigs taken out of the jig accommodating box conform to the data table for electric/electronic device (preferably data table for circuit board) preferably selected by an operator in accordance with a detection signal from the jig detecting means, wherein the calculating portion starts a measurement process only when a verification result by the verifying means shows conformity.

A situation where the measurement is made with the taken-out jigs and the data table for circuit board selected by the operator left at variance with each other can be prevented.

Preferably, a driving or movement source for displacing or moving the jigs is or comprises a pulse motor and the displacement amount measuring means measures or identifies or detects a pulse number given to the pulse motor and obtains the displacement amount of the jigs from the pulse number.

As compared to a case where a spring compressible as the jigs are displaced is provided as the displacement amount measuring means and the displacement amount of the jigs is obtained from a compressed amount of this spring, it is not necessary to compress the spring and to give a force against a biasing force of the spring in the present invention. Thus, a value of the drag obtained by the measurement apparatus as a drag measuring means can be made more precise.

Further preferably, an escaping space is defined or left between the two jigs when the target position is reached.

Even if dusts or the like should be attached to the jigs, such dusts are located in the escaping space. Thus, the jigs can be securely displaced to the target position. Therefore, measurement values such as the drag can be given with high precision.

Still further preferably, the jigs include a fixed jig and a movable jig relatively displaceable toward and away from the fixed jig, and/or the measuring apparatus further comprises a terminal holding portion capable of holding the press-fit terminal and displacing the press-fit terminal as the movable jig is displaced or moved.

The terminal holding portion can move the press-fit terminal as the movable jig is displaced.

According to a further preferred embodiment of the invention, each jig is integrally or unitarily provided with at least a large-diameter jig and a small-diameter jig so that at least two substitution holes can be formed or defined.

Operations such as attachment and detachment of the jigs can be reduced, thereby improving operability.

Preferably, a plurality of kinds of jigs are prepared in correspondence with conditions such as the specification of the electric/electronic device, preferably the circuit board, and the measuring apparatus further comprises: a jig accommodating box provided with one or more accommodating chambers for at least partly accommodating the respective jigs, a jig detecting means provided in correspondence with the respective jigs for detecting whether or not the respective jigs are at least partly accommodated in the accommodating chambers, and a verifying means for verifying whether or not the jigs taken out of the jig accommodating box conform to the data table for the electric/electronic device (preferably the data table for circuit board) preferably selected by an operator in accordance with a detection signal from the jig detecting means, wherein the calculating portion starts a measurement process only when a verification result by the verifying means shows conformity.

A situation where the measurement is made with the taken-out jigs and the data table for electric/electronic device (preferably circuit board) selected by the operator left at variance with each other can be prevented.

Further preferably, the jigs and the accommodating chambers comprise identification recess/projection means which are engageable with each other to permit the accommodation of the jigs in the case of a correct combination of the jigs and the accommodating chamber while being not engageable to prevent the jigs from being properly accommodated in the case of a wrong combination.

A situation where the jigs are accommodated in wrong accommodating chambers can be prevented.

Still further preferably, the press-fit terminal is set at a position corresponding to any one of the respective substitution holes in the jigs, and/or the measuring apparatus further comprises: a terminal detecting means for detecting the press-fit terminal, and a verifying means for verifying whether or not the substitution hole corresponding to the set position of the press-fit terminal conforms to the data table for the electric/electronic device (preferably the data table for circuit board) selected by an operator in accordance with a detection signal from the terminal detecting means, wherein the calculating portion starts a measurement process only when a verification result of the verifying means shows conformity.

A situation where the measurement is started with the press-fit terminal set at the position corresponding to a wrong substitution hole can be prevented.

Most preferably, the jigs are relatively displaced in separating directions after being moved closer to the press-in portion to at least partly squeeze or urge or deform the press-in portion, and the displacement amount measuring means measures the displacement amount of the jigs and/or the load measuring means measures the load also when the jigs are relatively displaced in the separating directions, wherein the displacement amount of the jigs is calculated until the load substantially becomes 0.

The displacement amount of the jigs until the load substantially becomes 0 after the relative displacement of the jigs in separating directions is started is substantially equal to a resiliently restored amount of the squeezed press-in portion. Accordingly, the resiliently restored amount of the squeezed press-in portion can be obtained by the present invention.

Further preferably, there are further provided: a judging means for judging whether or not the displacement amount of the jigs lies within a judgment reference area saved in the storage to judge whether or not the press-fit terminal is good, and preferably a display for notifying a judgment result by the judging means to an operator.

Since the operator needs not judge whether or not the measured press-fit terminal is good, operability is better.

Further preferably, the jigs are relatively displaced in separating directions after being moved closer to the press-in portion to at least partly squeeze or deform or urge the press-in portion, the jigs are repeatedly moved closer to and away from the press-in portion or from each other, the load and the hole diameter between the two jigs obtained from the displacement amount during the repeated movements of the jigs are output, preferably written in the data table for terminal, and a terminal characteristic graph generated based on the data table for terminal is output, preferably displayed on a display.

If parts of the terminal characteristic graph displayed on the display corresponding to the movements of the jigs closer to and away from the press-in portion or from each other substantially overlap each other, it can be judged that the resiliency of the press-in portion is kept. In other words, the durability of the press-in portion can be known by the present invention.

Most preferably, the data table for electric/electronic device (preferably the data table for circuit board) and the data table for terminal are compared upon occasion in a measurement process, and the jigs are relatively displaced in separating directions when the data table for electric/electronic device (preferably the data table for circuit board) and the data table for terminal substantially reach a point of coincidence.

Since the obtained resiliently restored amount of the press-in portion can be made equivalent to the one obtained when the press-in portion is actually mounted into the hole of the circuit board, a value of the resiliently restored amount approximate to the one obtained at the time of actual mounting can be obtained.

According to a further preferred embodiment of the invention, the jigs include a fixed jig and a movable jig relatively displaceable toward and away from the fixed jig or movable relatively to each other, and the measuring apparatus preferably further comprises a terminal holding portion capable of holding the press-fit terminal and displacing the press-fit terminal as the movable jig is displaced.

The terminal holding portion can move the press-fit terminal as the movable jig is displaced.

Preferably, the terminal holding portion is detachably mountable on a movable portion movable as the movable jig is displaced, and comprises a locking member for locking the mounted terminal holding means, wherein the locking member can lock and unlock the terminal holding portion through one-touch operation e.g. by a bayonet lock.

Since the terminal holding portion can be mounted after the press-fit terminal is held by the terminal holding portion outside, an operation of mounting and detaching the press-fit terminal can be easier. In addition, since the terminal holding portion can be attached and detached through one-tough operation of the locking member, operability is better.

Further preferably, there is further provided a jig locking member for holding the jigs in their mounted state, and the jig locking member can lock and unlock the jigs through one-touch operation.

The jigs can be easily mounted and detached, thereby presenting good operability.

Still further preferably, a driving source for displacing the jigs is or comprises a pulse or step motor (being linear or non-linear) and the displacement amount measuring means measures a pulse or step number given to the pulse motor and obtains the displacement amount of the jigs from the pulse number.

As compared to a case where a spring compressible as the jigs are displaced is provided as the displacement amount measuring means and the displacement amount of the jigs is obtained from a compressed amount of this spring, it is not necessary to compress the spring and to give a force against a biasing force of the spring in the present invention. Thus, a value of the drag obtained by the measuring apparatus as a drag measuring means can be made more precise.

Most preferably, an escaping space is defined between the two jigs when the target position is reached.

Even if dusts or the like should be attached to the jigs, such dusts are located in the escaping space. Thus, the jigs can be securely displaced to the target position. Therefore, measurement values such as the drag can be given with high precision.

According to the invention, there is further provided a measuring or detecting method, in particular using the measuring apparatus according to the invention or a preferred embodiment thereof, for obtaining a drag or retaining force acting when a press-in portion of a press-fit terminal is at least partly pressed into or engaged with a hole or recess of an electric device such as a circuit board to be held by being squeezed or deformed and substantially widening or deforming the hole, comprising the following steps: relatively displacing at least one pair of jigs to hold the press-in portion from substantially opposite sides along a direction at an angle different from 0° or 180°, preferably substantially normal to the longitudinal direction of the press-in portion, thus forming or defining a substitution hole having a dimension substantially corresponding to a hole diameter of the hole when a target position is reached, measuring or detecting a (relative) displacement amount of the jigs, measuring a load acting on the jigs from the press-in portion when the jigs are moved closer to the press-in portion, storing a data table for electric device, preferably a data table for circuit board, written with a load necessary to widen the hole of the electric device, preferably the circuit board, and the hole diameter of the widened hole, and outputting or writing the measured load and the hole diameter between the two jigs obtained from the measured displacement amount of the jigs and calculating a load at a point of coincidence of the data table for terminal and the data table for electric/electronic device, preferably circuit board.

According to a preferred embodiment of the invention, the measuring method further comprises a step of judging whether or not the load at the point of coincidence of the two data tables lies within a judgment reference range saved in the storage to judge or discriminate whether or not the press-fit terminal is good, and preferably notifying a judgment result by the judging means to an operator.

According to the invention, there is further provided a computer program product, in particular stored on a computer-readable storage medium, comprising computer-readable instructions which when loaded on a computer performs or controls a measuring method according to the invention or a preferred embodiment thereof.

These and other objects, features and advantages of the present invention will become more apparent upon reading of the following detailed description of preferred embodiments and accompanying drawings. It should be understood that even though embodiments are separately described, single features thereof may be combined to additional embodiments.

BRIEF DESCRIPTION OF THE DRAWINGS

FIG. 9 is a diagram showing a data table.

FIG. 22 is a table listing initial conditions.

DETAILED DESCRIPTION OF THE PREFERRED EMBODIMENTS

A first preferred embodiment of the present invention is described with reference to FIGS. 1 to 11.

Figure 1A:
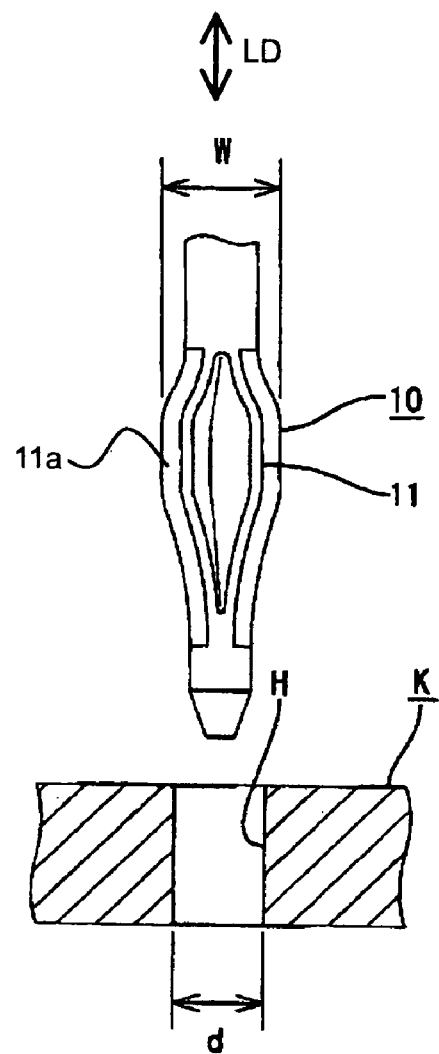
FIG. 1(A) is a section showing a state before a press-in portion of a press-fit terminal is pressed into a hole of a circuit board according to a first embodiment of the invention and FIG. 1(B) is a section showing a state where the press-in portion of the press-fit terminal is pressed into the hole of the circuit board according to the first embodiment of the invention.
Figure 1B:
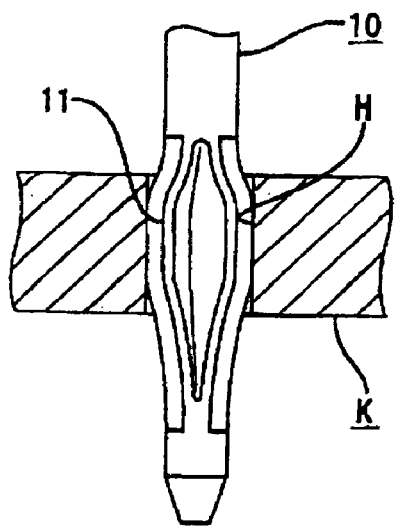

First, a press-fit terminal 10 includes an insertion or press-in portion 11 having a plurality of press-in parts 11a being deformable which can be at least partly inserted or fitted or pressed into a hole or recess H (being preferably substantially round) of a circuit board K (as a preferred electric or electronic device) as shown in FIG. 1(A). This press-in portion 11 has a laterally long and substantially S- or Z- or N-shaped cross section (see FIG. 3) and is at least partly squeezed or compressed by the wall of the hole H as being pressed into the hole H as shown in FIG. 1(B), thereby undergoing such a deformation as to reduce diameter or width W (or a dimension in a direction substantially normal to a longitudinal direction LD of the press-in portion 11 or an outer dimension of a cross section of the press-fit terminal 10 taken in a direction lying in the plane of the hole H or the circuit board K, e.g. horizontal dimension shown in FIG. 1). During this press-in operation, the hole H is widened by the press-in portion 11 to undergo such a deformation as to increase a hole diameter d. A measuring apparatus of this embodiment is designed to obtain a drag acting with the press-in portion 11 held in the hole K. This drag is a force acting on the hole H of the circuit board K in a direction normal to vertical direction (or the longitudinal direction LD of the press-in portion 11) with the press-in portion 11 at least partly pressed in the hole H, i.e. a force contributing to preventing the press-in portion 11 from coming out of the hole H.

This measuring apparatus is roughly comprised of a testing unit 20 for conducting such a test as to squeeze the press-in portion 11 by means of jigs 21, a jig accommodating box 30 for at least partly accommodating the jigs 21 used in the test, and a control unit 40 for controlling the testing unit 20. In this measuring apparatus, preferably three kinds of jigs 21 are prepared in view of a tolerance range of the hole H. During a measurement, a plurality of press-fit terminals 10 arbitrarily selected e.g. from one lot are measured using these three kinds of jigs 21 to judge whether or not the press-fit terminals 10 are good or within a specified (predetermined or predeterminable) tolerance.

Figure 2:
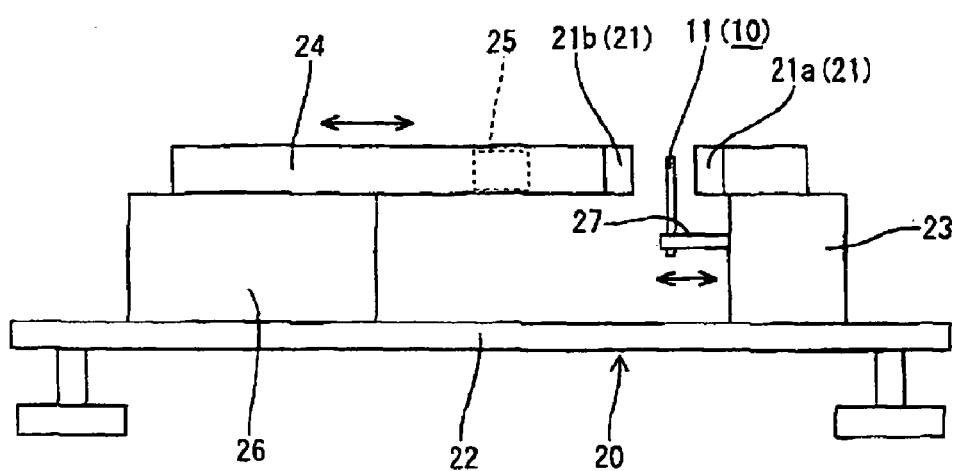
FIG. 2 is a side view schematically showing a testing unit.

As shown in FIG. 2, the testing unit 20 is provided with a pair of jigs 21 capable of holding or engaging the press-in portion 11 from substantially opposite sides substantially along horizontal direction (direction substantially normal to the longitudinal direction LD of the press-in portion 11), a pedestal 22, a fixing portion 23 fixed to the pedestal 22 and adapted to hold the fixed jig 21a at one side, a slide or movable table 24 for holding the movable jig 21b at the other side, a load cell 25 provided in or corresponding to the slide table 24, a pulse motor 26 (as a preferred movement means) fixed to the pedestal 22 and adapted to displace the slide table 24, and a terminal holding portion 27 provided on or corresponding to the fixing portion 23 and capable of detachably holding or positioning the press-in terminal 10.

Figure 3A:
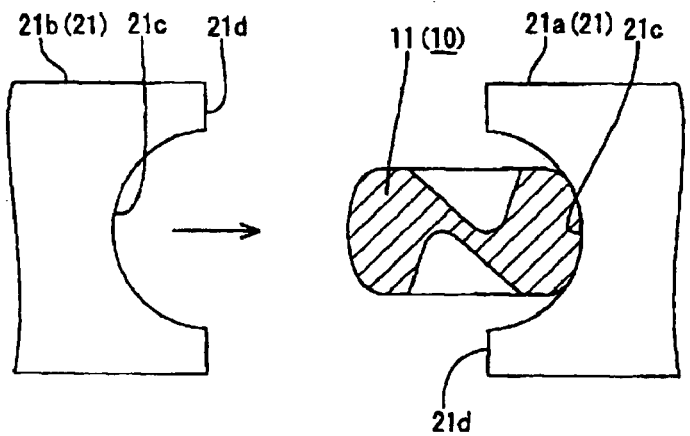
FIG. 3(A) is a plan view in section showing a state where a movable jig is located at an initial position.
Figure 3B:
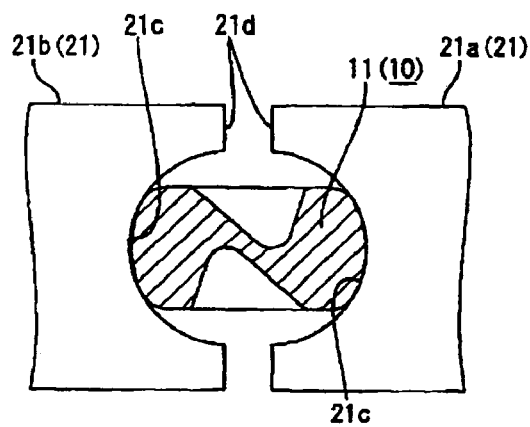
FIG. 3(B) is a plan view in section showing a state where the movable jig is in contact with the press-in portion.
Figure 3C:
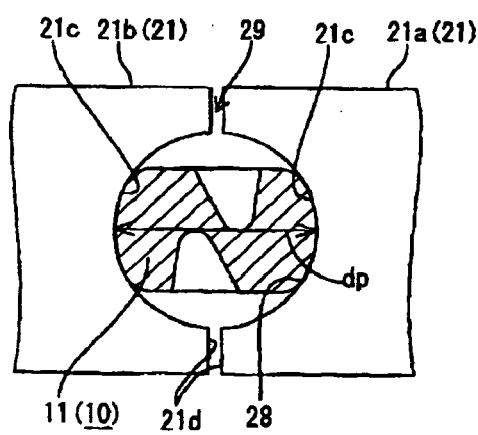
FIG. 3(C) is a plan view in section showing a state where a substitution hole is formed by two jigs.

The jigs 21 are relatively displaceably mounted such that the movable jig 21b is movable toward and away from the fixed jig 21a substantially along horizontal direction (or a direction substantially normal to the longitudinal direction LD). The thickness of the jigs 21 preferably is set to be substantially equal to that of the circuit board K. A recess 21c having a shape substantially corresponding to half of that of the hole H (preferably a substantially semicircular cross section) is formed in each of the substantially facing surfaces of the jigs 21a, 21b as shown in FIG. 3(A). When the movable jig 21b reaches a position shown in FIG. 3(C), a space substantially corresponding to the hole H (preferably a substantially circular space) is formed between or by the two jigs 21a, 21b. A diameter of this space has such a dimension substantially corresponding to the diameter d of the hole H of the circuit board K. In other words, a substitution hole 28 substantially equivalent or corresponding to the hole H can be formed between or defined by the two jigs 21a, 21b. During a measurement, the movable jig 21b is displaced from an initial position shown in FIG. 3(A) toward a target position where the movable jig 21b forms the substitution hole 28 in cooperation with the fixed jig 21a. The two jigs 21a, 21b preferably are set such that leading end portions 21d thereof are spaced apart by a specified (predetermined or predeterminable) distance when the movable jig 21b reaches the target position to form or define the substitution hole 28. In other words, an escaping space 29 (FIG. 3(C)) preferably is defined between the facing leading end portions 21d of the two jigs 21a, 21b. Thus, even if dusts or the like are attached to a certain extent to the leading end portions 21d of the two jigs 21a, 21b, the movable jig 21b can be securely moved to the target position where the substitution hole 28 is formed. Further, the two jigs 21a, 21b preferably are detachably held onto the slide table 24 and the fixing portion 23, respectively.

Figure 4:
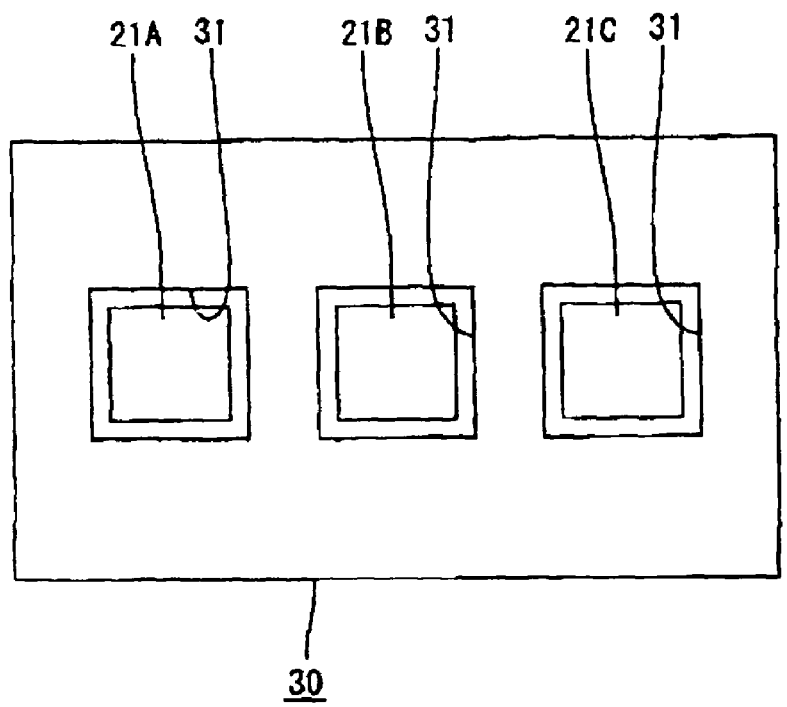
FIG. 4 is a plan view schematically showing a jig accommodating box.

There are prepared a plurality of jigs having different substitution hole diameters, preferably three kinds of jigs 21: standard-diameter jigs 21A capable of forming the substitution hole 28 having a dimension corresponding to a standard hole diameter d0 of the hole H, large-diameter jigs 21B capable of forming the substitution hole 28 having a dimension corresponding to a maximum value dmax of a tolerance range of the hole diameter of the hole H; and small-diameter jigs 21c capable of forming the substitution hole 28 having a dimension corresponding to a minimum value dmin of the tolerance range of the hole diameter of the hole H (see FIG. 4). These three kinds of jigs 21A, 21B, 21C preferably are differently marked (e.g. colored in different colors) so as to be distinguishable from each other.

As shown in FIG. 2, the terminal holding portion 27 can tightly hold the press-fit terminal 10 at its part lower or other than or substantially opposite to the press-in portion 11 laterally (a direction substantially normal to the longitudinal direction LD of the terminal 10) or from substantially opposite sides (preferably substantially along horizontal direction) such that the press-in portion 11 is located preferably above and the longitudinal direction LD thereof preferably is substantially aligned with vertical direction. The terminal holding portion 27 is so assembled with the fixing portion 23 by an unillustrated self-aligning mechanism as to be relatively displaceable substantially along horizontal direction or in a plane substantially parallel to the plane containing the substitution hole 28 or the jigs 21. Accordingly, the terminal holding portion 27 is or can be displaced in the substantially same direction as the movable jig 21b as the press-in portion 11 is pushed by the movable jig 21b (substantially following the movement of the press-in portion 11 pushed by the movable jig 21b). This terminal holding portion 27 preferably is provided with a positioning means (not shown) for positioning the press-fit terminal 10 with respect to the jigs 21 along the longitudinal direction LD of the press-fit terminal 10. Accordingly, if the press-in portion 11 is formed at its proper position during the molding or forming of the press-fit terminal 10, the press-in portion 11 can be squeezed by the jigs 21 in the same manner as when the press-in portion 11 is pressed into the hole H of the circuit board K. It should be noted that the press-fit terminal 10 to be measured has a portion thereof unnecessary for the measurement preferably eliminated or cut off, i.e. includes only the press-in portion 11 and a portion to be tightly held by the terminal holding portion 27.

The slide table 24 and the pulse motor 26 are connected via an unillustrated torque transmitting mechanism. The slide table 24 is transversely displaceable substantially along horizontal direction or substantially normal to the longitudinal direction LD, i.e. toward and away from the fixing portion 23 by transmitting the rotation of the pulse motor 26 to the slide table 24. The slide table 24 is provided with the load cell 25 for measuring a force received by the movable jig 21b. The pulse motor 26 and the load cell 25 are connected with the control unit 40 to be described later. Further, the pulse motor 26 is driven in accordance with a pulse signal inputted from an unillustrated driving circuit preferably controlled by the control unit 40.

As shown in FIG. 4, the jig accommodating box 30 includes a plurality of (e.g. three) accommodating chambers 31 for individually at least partly accommodating the plurality of (e.g. three) kinds of jigs 21A, 21B, 21C. Each accommodating chamber 31 is marked (e.g. colored) in conformity with the jigs 21 to be at least partly accommodated therein in order to prevent the error accommodation of the jigs 21 into the accommodating chambers 31. Upon a measurement, the desired jigs 21 are taken out of the jig accommodating box 30 and mounted on the slide table 24 and the fixing portion 23 of the testing unit 20. A plurality of switches 32 corresponding to the respective jigs 21A, 21B, 21C are provided in the respective accommodating chambers 31 and connected with the control unit 40 to be described later 40 (see FIG. 5).

Figure 5:
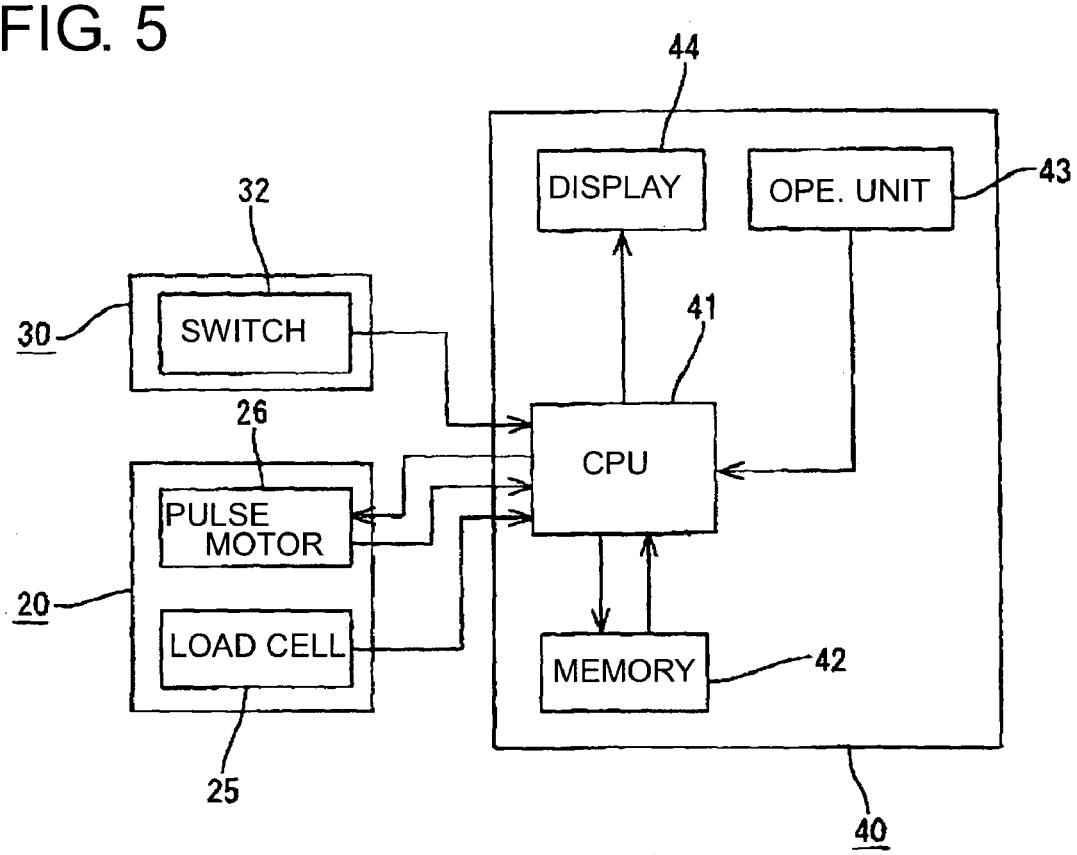
FIG. 5 is a block diagram showing a relationship of a control unit, the testing unit and the jig accommodating box.

As shown in FIG. 5, the control unit 40 is provided with a CPU 41 for signal processing, a memory 42 for saving data, an operation unit 43 for inputting or giving instructions to the CPU 41, and a display 44 (as a preferred output device) for outputting (preferably displaying) one or more measurement results and the like inputted from computed by the CPU 41.

Figure 6:
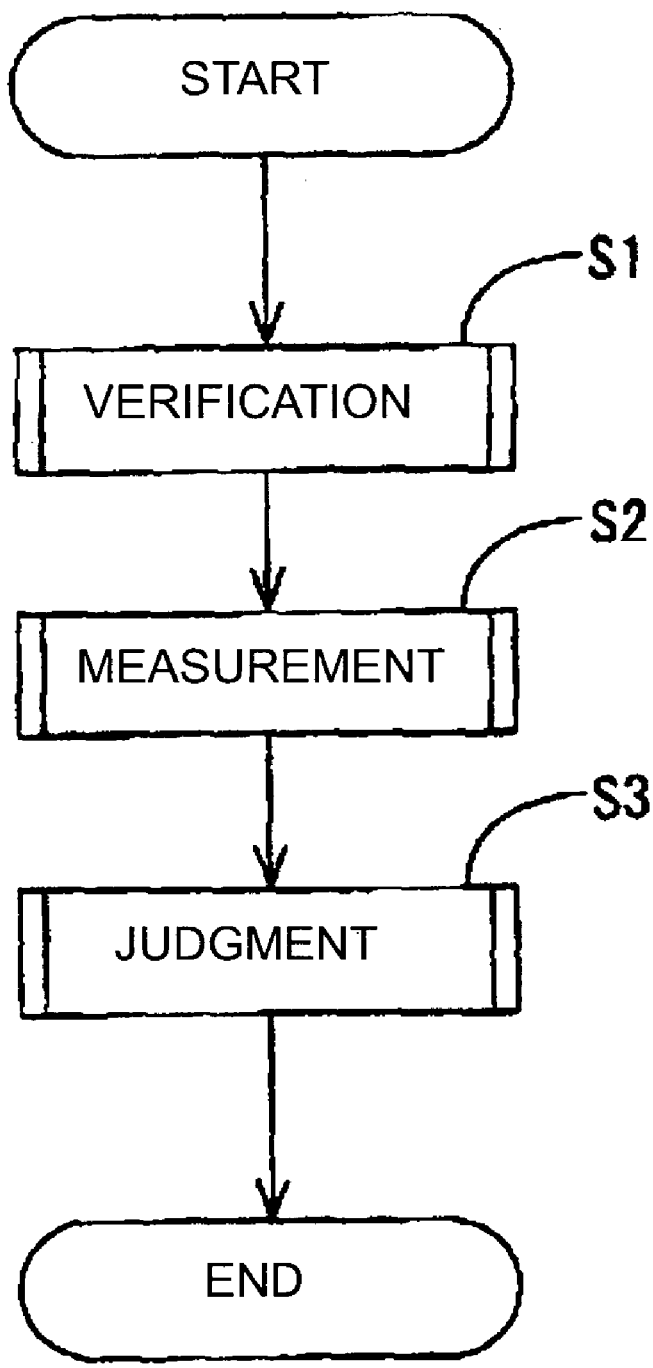
FIG. 6 is a flow chart showing the control of a CPU.

The control of the CPU 41 includes, as shown in FIG. 6, a first operation of verifying whether or not the jigs 21 taken out of the jig accommodating box 30 conform to data (such as a file or table or list) called from the operation unit 43 (Step S1), a successive operation of squeezing or pressing the press-in portion 11 by means of the jigs 21 and detecting the amount of squeezing (preferably measuring a hole diameter between the two jigs 21a, 21b) and/or measuring a load (drag) (Step S2), and a final operation of judging whether or not a measurement result satisfies specific (predetermined or predeterminable) judgment criteria (Step S3). Flow charts of the respective operations are described in detail below.

Figure 7:
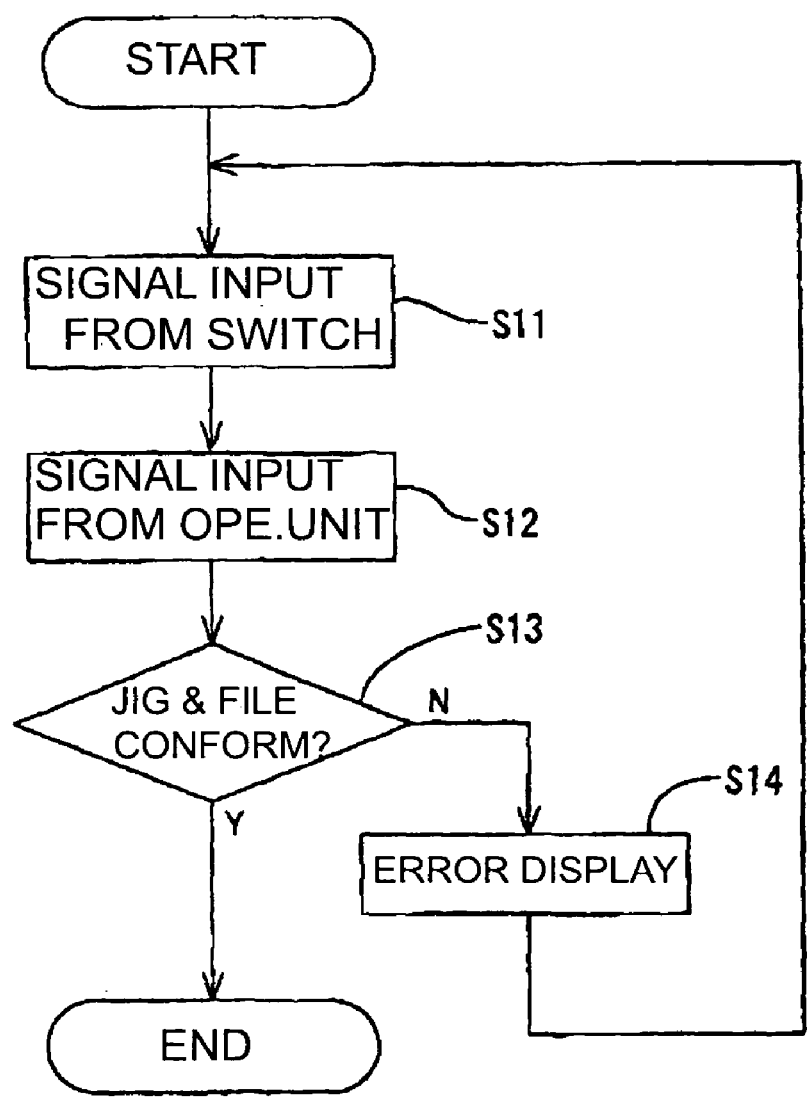
FIG. 7 is a flow chart showing a verification process.

As shown in FIG. 7, when the jigs 21 are taken out of the accommodating chamber 31 of the jig accommodating box 30, a signal is inputted to the CPU 41 from the switch 32 corresponding to these jigs 21 (Step S11). When a specified (predetermined or predeterminable) file or data is/are inputted or called by operating the operation unit 43, a signal corresponding to this file/these data is inputted to the CPU 41 (Step S12). It should be noted that this file/these data is/are used during the succeeding judgment process and prepared in correspondence with each kind of jigs 21. The file/data is/are described in detail later. Whether or not the taken-out jigs 21 and the called file conform or are correctly corresponding to each other is judged by the PCU 41 (Step S13). An error output such as an error display (e.g. characters saying "jigs and file do not conform") is made on the display 44 (Step S14) if the judgment result is negative. Thus, after the jigs 21 and/or the file are replaced by the proper one(s), signals from the switch 32 and the operation unit 43 are verified again. If the judgment result is positive, the verification process is completed, followed by the succeeding measurement process. An error output such as an error display is made also when more than two jigs 21 are taken out.

Figure 8:
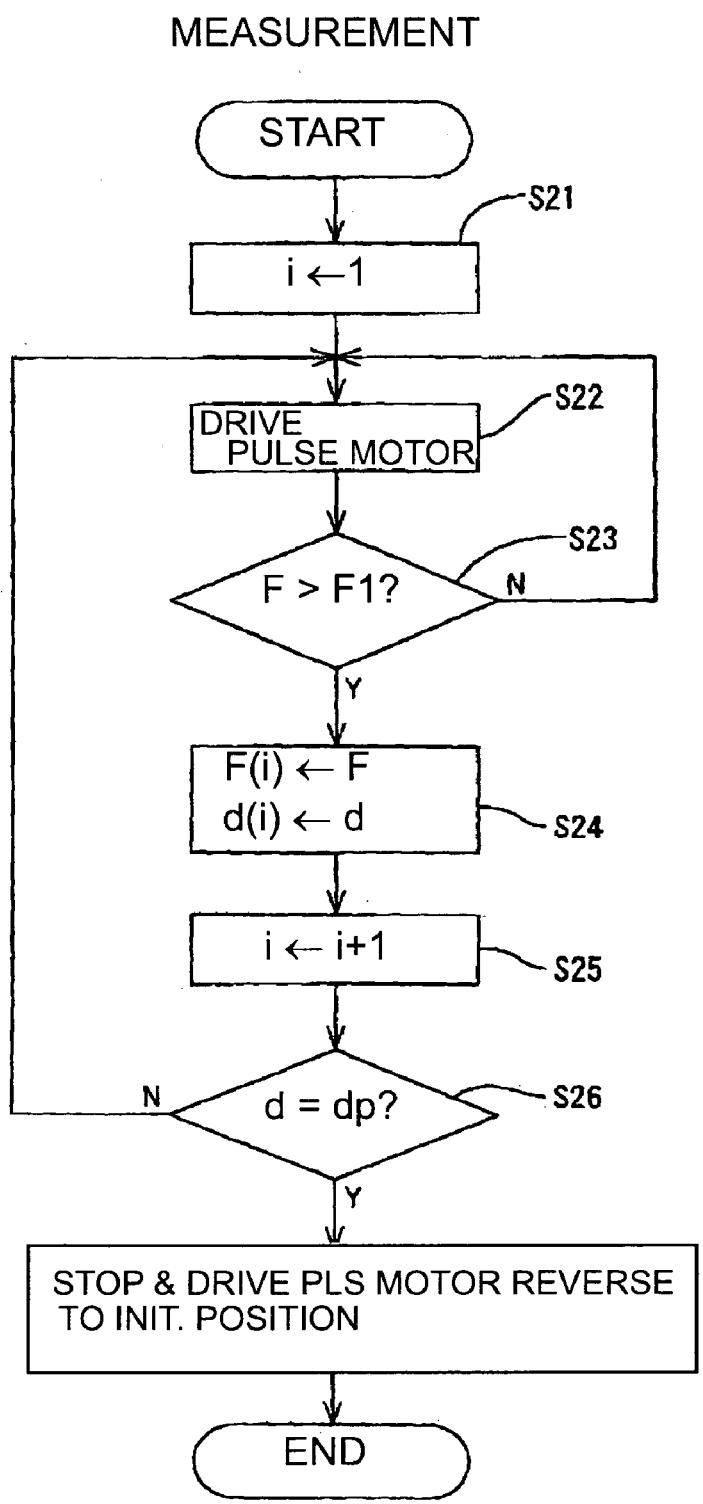
FIG. 8 is a flow chart showing a measurement process.
Figure 9:
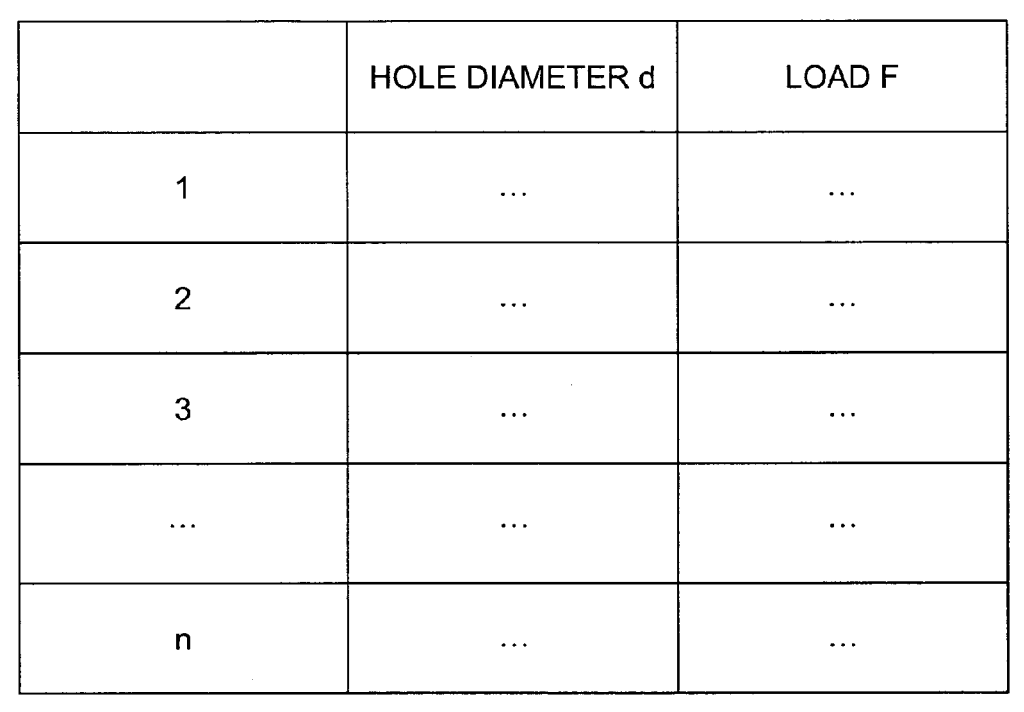

After completing the verification process, the measurement or detection process shown in FIG. 8 is carried out. The pulse motor 26 (as a preferred movement means) is driven (Step S22) to bring or move the movable jig 21b toward the fixed jig 21a. When the movable jig 21b starts contacting the press-in portion 11 (see FIG. 3(B)) and a load exceeds a measurement-start reference value F1 (Step S23), a displacement amount of the movable jig 21b is obtained preferably from a pulse number (as a preferred movement amount value) given to the pulse motor 26 and the hole diameter d between the two jigs 21a and 21b calculated based on the obtained displacement amount and/or a load F calculated from an input signal from the load cell 25 are written in the data table for terminal (Step S24). Whether or not the hole diameter d has reached a target value dp (hole diameter when the substitution hole 28 is formed) is judged (Step S26), and the hole diameter d and the load F continue to be detected and/or written if the judgment result is negative. At this time, data are written from the first to n-th arrays of the data table for terminal as shown in FIG. 9 (Steps S21, S25). This data table for terminal may be saved in the memory 42 upon occasion or a terminal characteristic graph TG may be generated based on the respective data and outputted (e.g. displayed on the display 44) upon occasion or request (see FIG. 11).

The measurement is completed if the hole diameter d has reached the target value dp. The pulse motor 26 is driven in a direction opposite from the one during the measurement after being temporarily stopped, whereby the movable jig 21b is returned toward or to the initial position to prepare for a measurement of a next press-fit terminal 10 (Step S27). This target value dp is d0 when the jigs 21 used are the standard diameter jigs 21A; dmax when they are the large-diameter jigs 21B; and dmin when they are the small-diameter jigs 21C (See FIG. 11). If the measured load F exceeds a specified (predetermined or predeterminable) value preferably an assumed upper limit value (e.g. a value of a load above which the measuring apparatus may be damaged), the pulse motor 26 may automatically stop.

Figure 10:
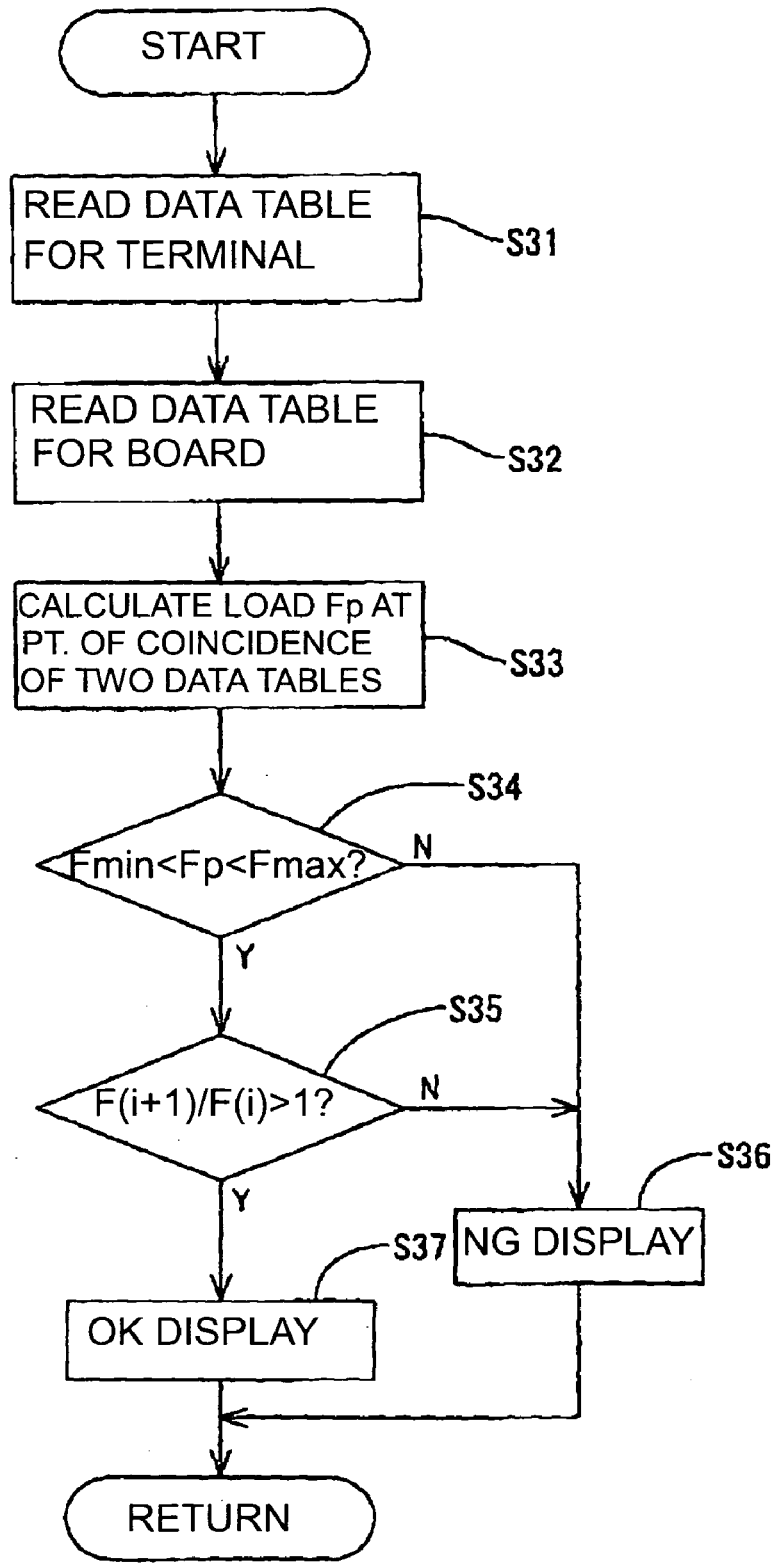
FIG. 10 is a flow chart showing a judgment process.

Upon completing the measurement or detection, the judgment process shown in FIG. 10 is carried out. During the judgment process, the data table for terminal containing or having the measurement result written therein is read (Step S31), a data table for circuit board (see FIG. 9) generated by obtaining a relationship between the load F necessary to push and widen the hole H of the circuit board K and the widened hole diameter d obtained preferably by means of CAE (computer aided engineering) is read (Step S32), and a load Fp preferably at a point of coincidence of the two data tables is calculated (Step S33).

Figure 11:
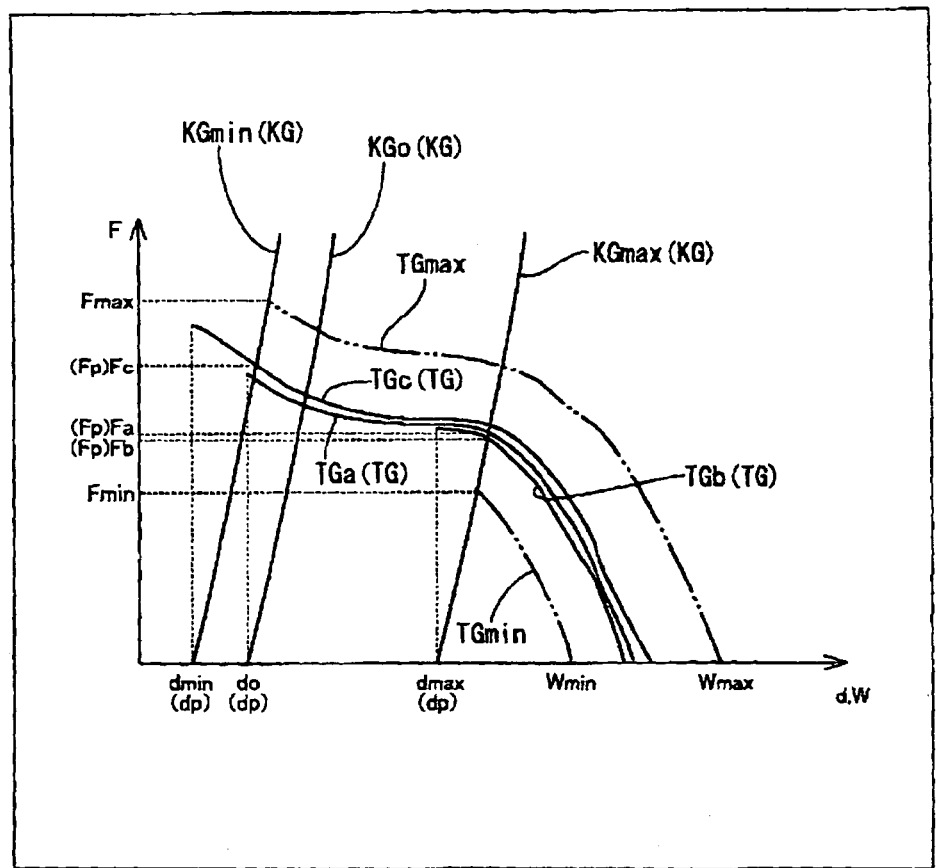
FIG. 11 is a graph showing one example of a display mode of a display.

There are a plurality of (preferably three) kinds of data tables for circuit board saved in the memory 42; a standard-diameter data table obtained by setting the standard value d0 as the hole diameter at a starting point (see board characteristic graph KG0 of FIG. 11), a large-diameter data table obtained by setting the maximum value dmax of the tolerance as the hole diameter at the starting point (see board characteristic graph Gmax of FIG. 11), and a small-diameter data table obtained by setting the minimum value dmin of the tolerance as the hole diameter at the starting point (see board characteristic graph Gmin of FIG. 11). The large-diameter data table and the small-diameter data table are related to corresponding (three) kinds of files selected during the verification process described above. More specifically, a file for the large-diameter jigs 21B and a file for the standard-diameter jigs 21A are related to the large-diameter data table, and a file for the small-diameter jigs 21C is related to the small-diameter data table. In other words, the data table for circuit board used during the judgment process is selected by selecting the file during the verification process. During this judgment process, the data table for circuit board related to the file (corresponding to the jigs) is read to be compared with the data table for terminal (Step S32). In the case of graph-representing the two data tables, the point of coincidence of the two data tables is an intersection of the two graphs TG, KG as shown in FIG. 11. Specifically, the point of coincidence is an intersection of a terminal characteristic graph TGa and a board characteristic graph KGmax when the jigs 21 used for the measurement were the standard-diameter jigs 21A; an intersection of the terminal characteristic graph TGb and a board characteristic graph KGmax when the jigs 21 used for the measurement were the large-diameter jigs 21B; and an intersection of the terminal characteristic graph TGc and a board characteristic graph KGmin when the jigs 21 used for the measurement were the standard-diameter jigs 21C. At the respective points of coincidence, loads Fa, Fb, Fc can be obtained. Further, when the measurement is made using the standard-diameter jigs 21A, a load at an intersection of the terminal characteristic graph TGa and the board characteristic graph KG0 can be obtained. In the respective data tables for circuit board, the load F tends to constantly increase as the hole diameter d increases as shown in FIG. 11. The standard value d0 of the hole diameter is a set value not including a processing error upon producing the circuit board K, i.e. a target value of the hole diameter during the production of the circuit board K. The data table for circuit board may be also obtained by a method other than the CAE (e.g. actual measurement, finite element simulation, etc.) or a combination thereof.

Whether or not the load Fp (Fa, Fb, Fc) at the point of coincidence of the two data tables lies within a judgment reference range saved or stored in the memory 42 is judged (Step S34). Specifically, judgment is made as to whether or not the load Fp at the point of coincidence is equal to or below an upper limit value Fmax of the judgment reference range and equal to or above a lower limit value Fmin of this range. If the load Fp is judged to lie beyond the judgment reference range, an according output is outputted, preferably a NG (not good) display (e.g. characters "NG") is displayed on the display 44 preferably to notify it to an operator (Step S36). This judgment reference range is defined between the upper limit value Fmax, which is a value of the load at the point of coincidence of the data table for terminal when the width of the press-in portion 11 of the press-fit terminal 10 takes an upper limit value Wmax of its tolerance range (see terminal characteristic graph TGmax of FIG. 11) and the data table for circuit board when the hole diameter takes a minimum value dmin of its tolerance (see board characteristic graph KGmin of FIG. 11), and the lower limit value Fmin, which is a value of the load at the point of coincidence of the data table for terminal when the width of the press-in portion 11 of the press-fit terminal 10 takes a lower limit value Wmin of its tolerance range (see terminal characteristic graph TGmin of FIG. 11) and the data table for circuit board when the hole diameter takes the maximum value dmax of its tolerance (see terminal characteristic graph TGmax of FIG. 11). In other words, if the measured load F should exceed the upper limit value Fmax of the judgment reference range, the drag of the press-in portion 11 becomes excessive to cause e.g. a crack, a warping, a damage or the like in the circuit board K. Conversely, if the measured load Fp falls below the lower limit value Fmin, the drag or holding force of the press-in portion 11 is insufficient and may cause the press-in portion 11 to come out of the hole H.

If the load Fp at the point of coincidence lies within the judgment reference range, judgment is successively made as to whether or not the measured load F is constantly increasing as the hole diameter d decreases (increase in the displacement amount of the movable jig 21b) (Step S35). Specifically, whether or not a value obtained by dividing a load F(i+1) of a next array by the load F(i) of a specified array exceeds 1 is judged. If the obtained value is smaller than 1, i.e. the load F is decreasing, a corresponding output is made, preferably a NG display (e.g. characters of "NG") is made on the display 44 (Step S36). If the obtained value is larger than 1, i.e. the load F is constantly increasing, a corresponding output is given, preferably an OK display (e.g. characters of "OK") is made on the display 44 preferably to notify it to an operator (Step S37). If the measured load F has decreased after an increase, there is a possibility that the press-in portion 11 is undergoing an improper deformation such as a buckling deformation and/or is damaged otherwise (e.g. one or more press-in parts 11a are damaged, bent or broken). The measured press-fit terminal 10 is judged to be good if a corresponding output, e.g. the OK display is made e.g. on the display 44 as above, whereas it is judged to be defect if a corresponding output, e.g. the NG display is made. If the judgment result shows that the measured press-fit terminal 10 is not good, there is a possibility that the width of the press-in portion 11 was erroneously set during the production of the press-fit terminal 10 or a wrong material was used for the press-fit terminal 10. Particularly, since the thickness of the jigs 21 is set to be substantially equal to that of the circuit board K and the press-fit terminal 10 is positioned with respect to the jigs 21 using the positioning means of the terminal holding portion 27 in this embodiment, there is also a possibility that the press-in portion 11 is formed at a position vertically (longitudinal direction LD) displaced from a proper position in the press-fit terminal 10 if the judgment result shows that the measured press-fit terminal 10 is not good.

Of course, it does not matter to judge as to whether or not the load Fp at the point of coincidence lies within the judgment reference area after judging whether or not the load F is on the increase. Further, as shown in FIG. 11, the terminal characteristic graphs TG (TGa, TGb, TGc) may be generated based on the data table for terminal, the board characteristic graphs KG (KG0, KGmax, Kgmin) may be generated based on the data table for circuit board, and these graphs are respectively displayed on the display 44. The operation unit 43 can be suitably controlled to instruct whether or not such an operation is necessary.

As described above, since the load (drag or force generating a resistance) of the press-in portion 11 is measured by the jigs 21 in this embodiment, no circuit board for testing needs to be prepared unlike a prior art measuring apparatus for measuring a holding force by actually mounting a press-in portion into the circuit board for testing. Thus, production costs can be reduced. Further, measurement values of higher precision can be obtained by using the jigs 21 as compared to the prior art measuring apparatus.

Further, the judgment reference range preferably is saved or stored in the memory 42, whether or not the load Fp at the point of coincidence of the data table for circuit board and the data table for terminal lies within the judgment reference range is judged by means of the CPU 41, and the judgment result is outputted, preferably displayed on the display 44 to notify it to the operator. Thus, the operator needs not judge whether or not the measured press-fit terminal 10 is good, which leads to better operability. Further, since the CPU 41 also judges whether or not the load F in the data table for terminal is constantly increasing as the hole diameter d decreases, whether or not the press-in portion 11 is properly deformed can also be judged. Furthermore, the display 44 preferably enables the operator to visually confirm the judgment result. Further, since at least one of the terminal characteristic graph TG generated based on the data table for terminal, the board characteristic graph KG generated based on the data table for circuit board and the judgment reference range (upper limit value Fmax and lower limit value Fmin) can be displayed on the display 44, the operator can be let to know developments of the measurement process and those of the judgment process.

Further, the large-diameter jigs 21B corresponding to the maximum value dmax of the tolerance of the hole diameter of the hole H and the small-diameter jigs 21C corresponding to the minimum value dmin of the tolerance of the hole diameter of the hole H are prepared as the jigs 21; the large-diameter data table obtained by setting the maximum value dmax of the tolerance of the hole diameter as the hole diameter at the starting point and the small-diameter data table obtained by setting the minimum value dmin of the tolerance of the hole diameter as the hole diameter at the starting point are prepared as the data tables for circuit board; and the CPU 41 calculates the load Fp at the point of coincidence of the data table for circuit board conforming to the selected jigs 21 and the data table for the measured terminal. Thus, a precise drag in view of the tolerance range of the hole H can be obtained. Further, in this embodiment, the standard-diameter jigs 21A corresponding to the standard value d0 of the hole diameter of the hole H and the standard-diameter data table obtained by setting the standard value d0 as the hole diameter at the starting point are prepared in addition to the other (e.g. two) kinds of jigs 21B, 21C and the data table for circuit board. Thus, a drag or retaining force which will act when the press-fit terminal 10 and the circuit board K are produced substantially without any processing error can be obtained.

Furthermore, a plurality of (e.g. three) kinds of jigs 21 preferably are at least partly accommodated in the accommodating chambers 31 of the jig accommodating box 30; the accommodation of the jigs 21 in the accommodating chambers 31 is individually detected by the detectors or switches 32; and the CPU 41 verifies whether or not the jigs 21 taken out of the accommodating chamber 31 and the file selected by the operator, i.e. the data table for circuit board conform in accordance with the detection signal from the switch 32 and transfers to the measurement process only when the jigs 21 and the data table for circuit board conform. Thus, a situation where the detection or measurement is made with the taken-out jigs 21 and the data table for circuit board selected by the operator left at variance with each other can be prevented, thereby improving operability.

Further, the pulse motor 26 is used as a preferred driving or movement source for displacing or moving the movable jig 21b, and the pulse number given to the pulse motor 26 is measured or detected as a preferred movement value and the displacement amount of the movable jig 21b is obtained from the measured pulse number. Thus, as compared to a case where a spring compressible as the jig is displaced is provided and a displacement amount of the jig is obtained from a compressed amount of the spring, it is not necessary to compress the spring and to give a force against a biasing force of the spring in this embodiment. Therefore, a value of the drag obtained by the load cell 25 can be made more precise.

Since the escaping space 29 preferably is defined between the two jigs 21a and 21b when the movable jig 21b reaches the target position, even if dusts or the like should be attached to the jigs 21a, 21b, they are located in the escaping space 29. Thus, the movable jig 21b can be securely displaced to the target position, with the result that the measurement values of the drag and the like can be highly precise. Further, by holding the press-fit terminal 10 using the terminal holding portion 27 free to displace along the displacing direction of the movable jig 21b, the press-fit terminal 10 can be displaced as the movable jig 21b is displaced.

A second preferred embodiment of the present invention is described with reference to FIGS. 12 to 31. It should be noted that no repetitive description is given on the construction of the second embodiment similar to or same as that of the first embodiment by identifying it by the same reference numerals.

Figure 12:
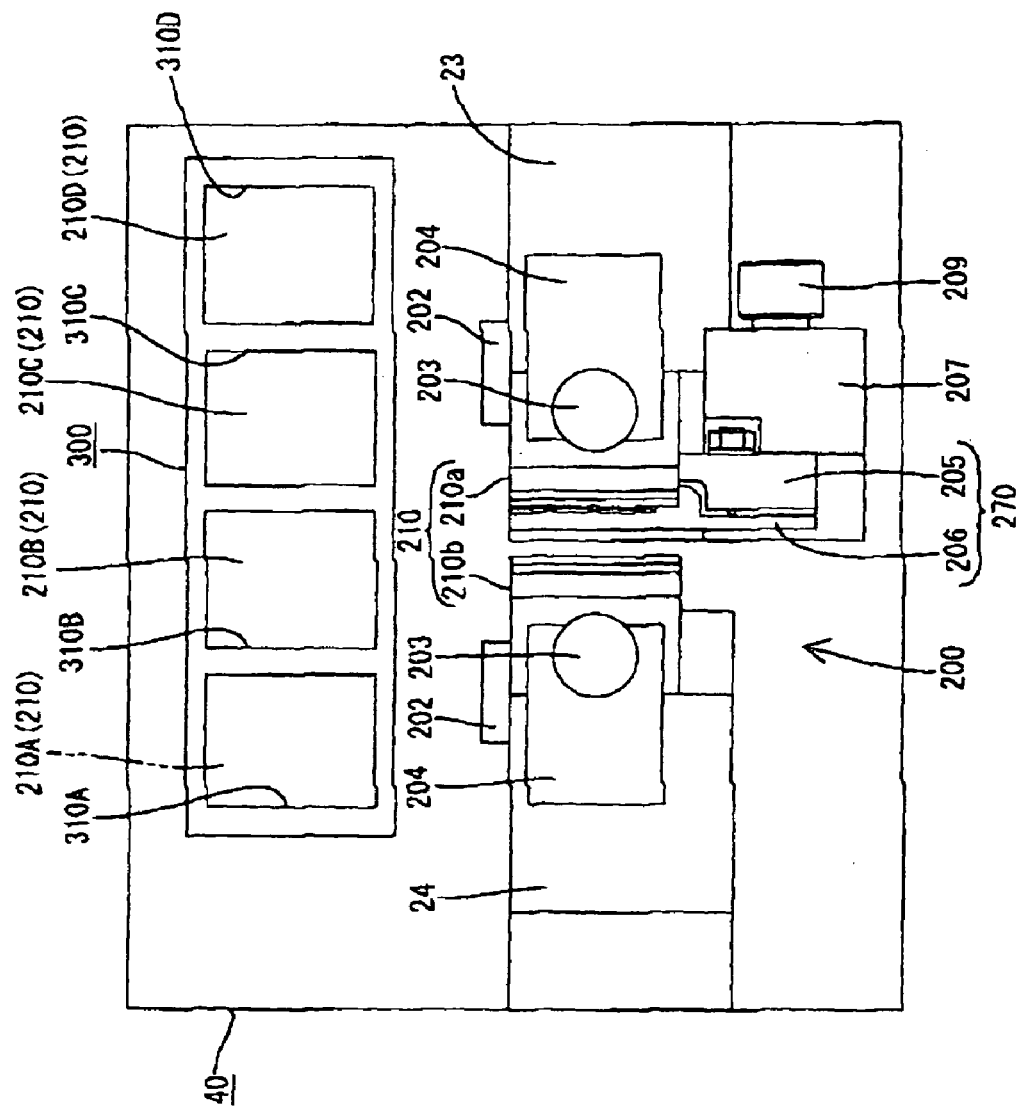
FIG. 12 is a plan view schematically showing a testing unit according to a second embodiment of the invention.
Figure 13:
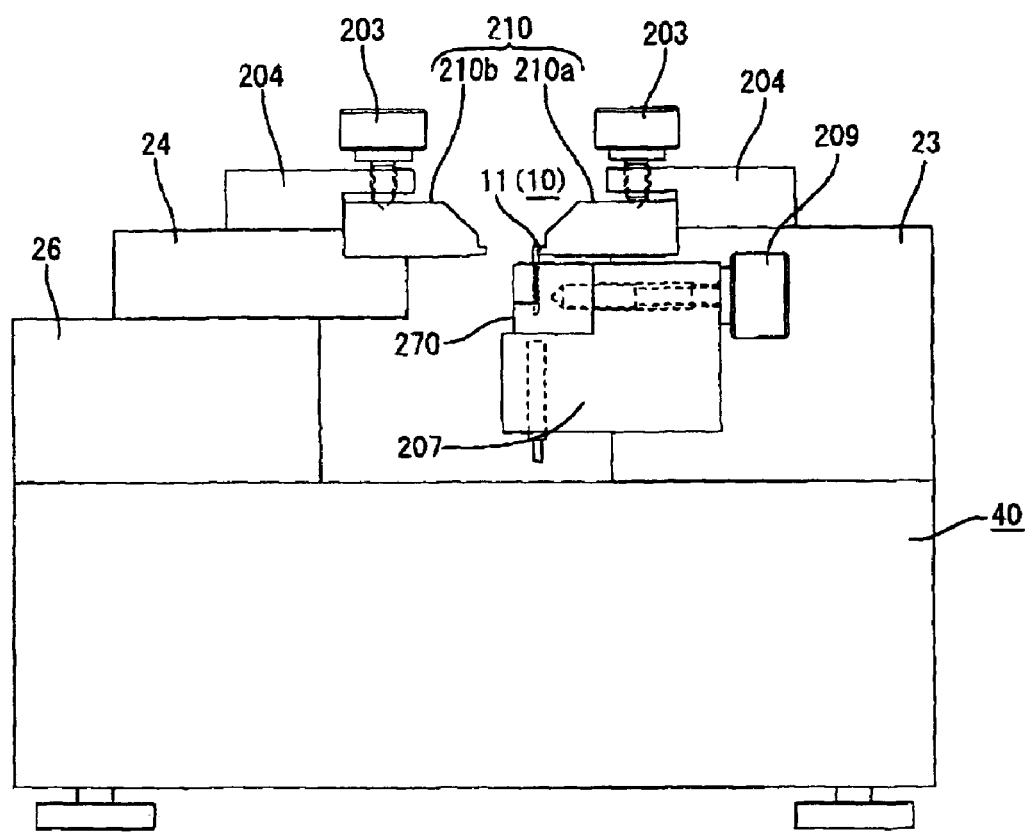
FIG. 13 is a side view schematically showing the testing unit.

As shown in FIGS. 12 and 13, this measuring apparatus is, roughly speaking, constructed such that a testing unit 200 and a jig accommodating box 300 are placed preferably on a lateral (upper) surface of a control unit 400 to be preferably integral to the control unit 400. In this measuring apparatus is used jigs 210 having a plurality of (e.g. three) kinds of recesses 210cA to 210cC in view of a tolerance range of a hole or recess H of a circuit board K (as a preferred electric or electronic device). Specifically, in the second embodiment, the three jigs shown in the first embodiment, i.e. the standard-diameter jig 21A, the large-diameter jig 21B and the small-diameter jig 21C are made into one jig 210 capable of forming a plurality of (e.g. three) substitution holes 280A to 280C. Further, a plurality of (e.g. four) kinds of jigs 210 corresponding to differences in the specifications of the circuit boards K (preferably differences in the size of the standard value d0 of the diameter of the hole H and/or the tolerance range and/or a difference in the material of the circuit board K) are prepared and at least partly accommodated in the jig accommodating box 300 to be described later. In the description below, suffixes A to D are attached to the reference numeral 210 of the respective jigs in the case of distinguishing the jigs 210 while no suffix is attached in the case of generally terming them without distinguishing.

Figure 14A:
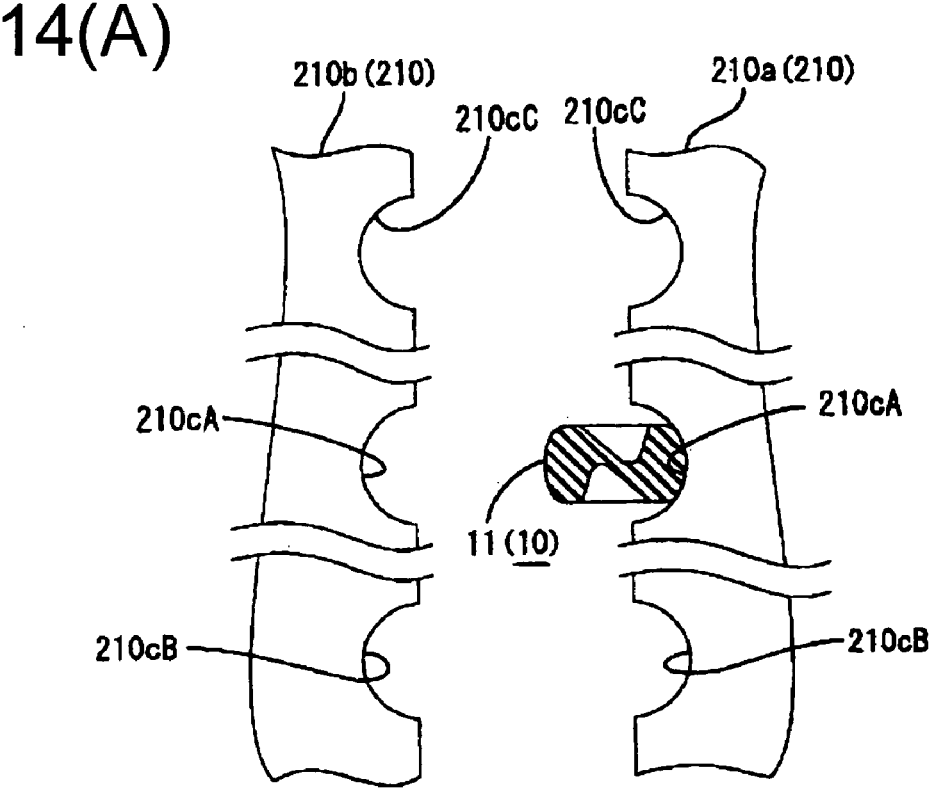
FIG. 14(A) is an enlarged plan view in section showing a state where a movable jig is located at an initial position and FIG. 14(B) is an enlarged plan view in section showing a state where substitution holes are formed by two jigs.
Figure 14B:
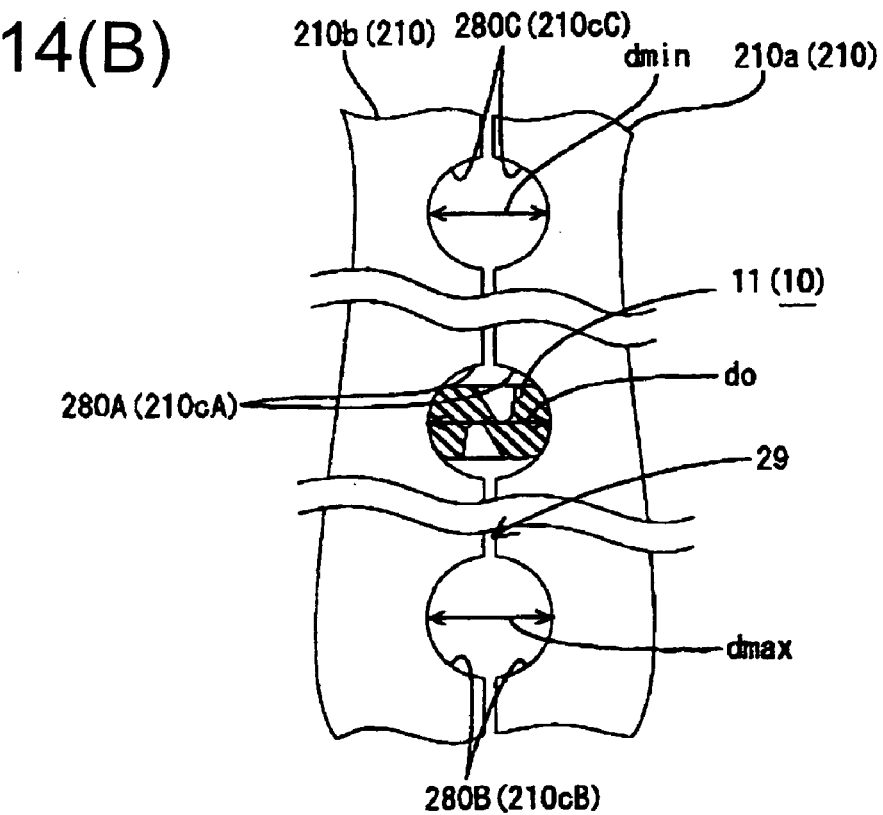

The jigs 210 include a fixed jig 210a mounted on a fixing portion 23 of the testing unit 200 and a movable jig 210b mounted on a slide table 24. As shown in FIG. 14(A), three preferably substantially semicircular recesses 210cA to 210cC having different sizes are formed substantially side by side along widthwise direction (longitudinal direction or a direction substantially normal to the moving direction of the movable jig 210b) in each of the substantially facing surfaces of the fixed jig 210a and the movable jig 210b, and three preferably substantially circular spaces, i.e. substitution holes 280A to 280C (having shapes substantially corresponding to the shapes of respective holes H) are substantially simultaneously defined between the two jigs 210a and 210b when the two jigs 210a, 210b reach a position (target position) shown in FIG. 14(B). More specifically, the standard-diameter recesses 210cA capable of forming the substitution hole 280A having a dimension substantially corresponding to the standard value d0 of the diameter of the hole H are provided preferably at intermediate positions (most preferably at substantially middle positions) of the fixed jig 210a and the movable jig 210b in FIGS. 14(A) and 14(B); the large-diameter recesses 210cB capable of forming the substitution hole 280B having a dimension substantially corresponding to a maximum value dmax of the tolerance range of the hole H are provided preferably at lateral (bottom) positions of the fixed jig 210a and the movable jig 210b in FIGS. 14(A) and 14(B); and the small-diameter recesses 210cC capable of forming the substitution hole 280C having a dimension substantially corresponding to a minimum value dmin of the tolerance range of the hole H are provided at opposite lateral (upper) positions of the fixed jig 210a and the movable jig 210b in FIGS. 14(A) and 14(B). Since the other constructions of the fixed jig 210a and the movable jig 210b and the escaping spaces 29 are same or similar as in the first embodiment, no description is given thereon. Further, only a case where the press-in portion 11 is located in the standard-diameter recesses 210cA in the middle is shown in FIGS. 14(A) and 14(B) without showing cases where the press-in portions 11 are located in the other two recesses 210cB, 210cC.

Figure 15:
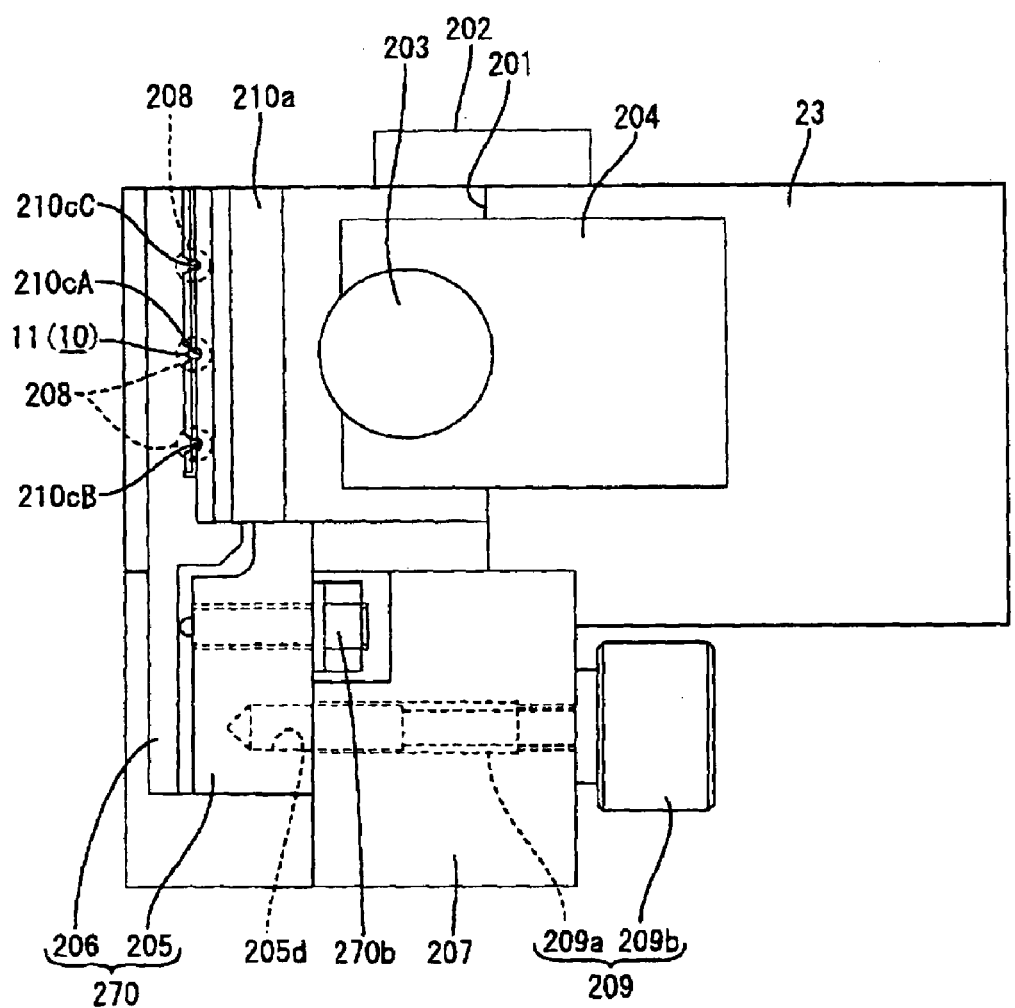
FIG. 15 is a schematic plan view of a side of a fixing portion.
Figure 16:
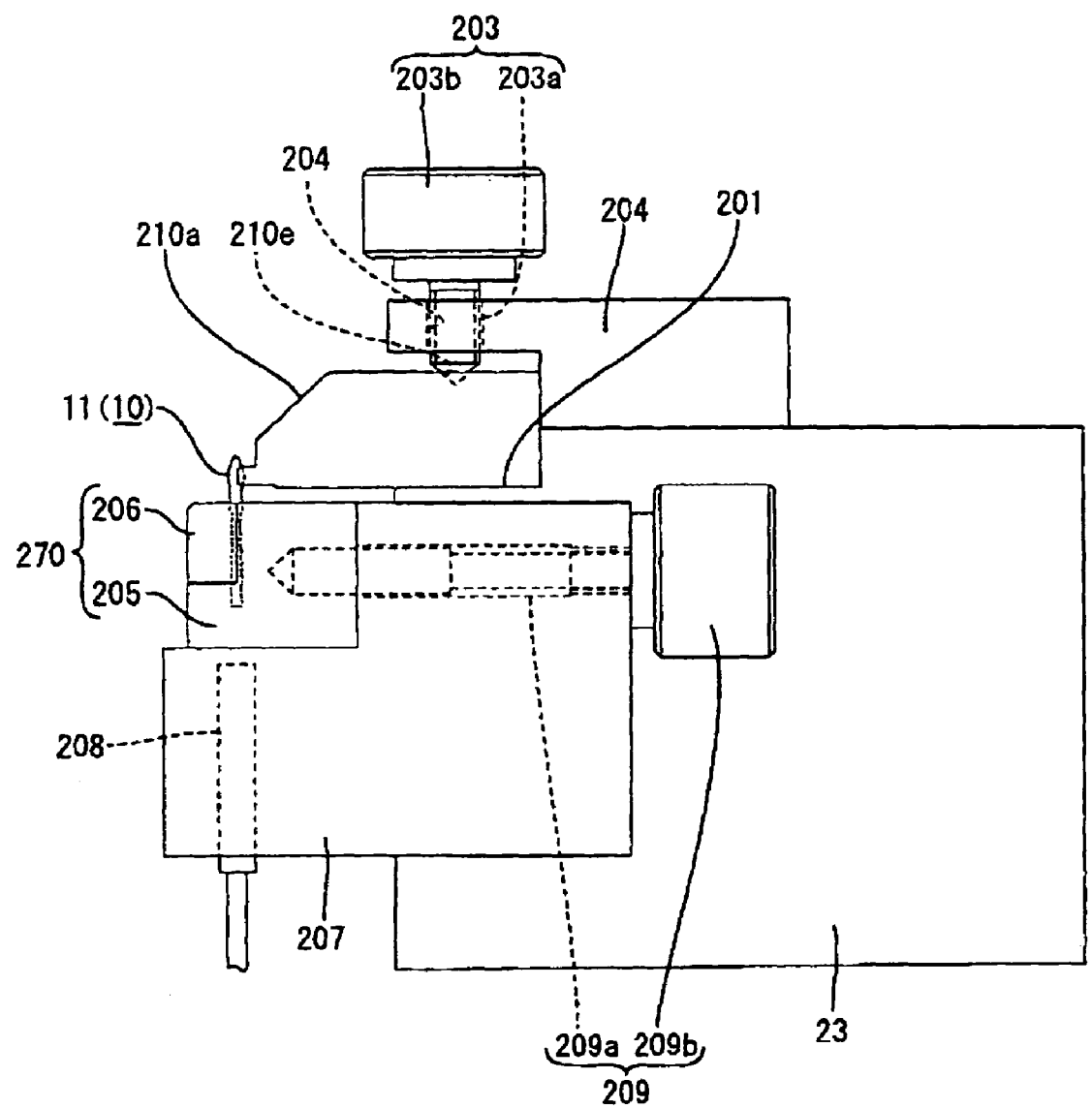
FIG. 16 is a schematic side view of the side of the fixing portion.
Figure 17:
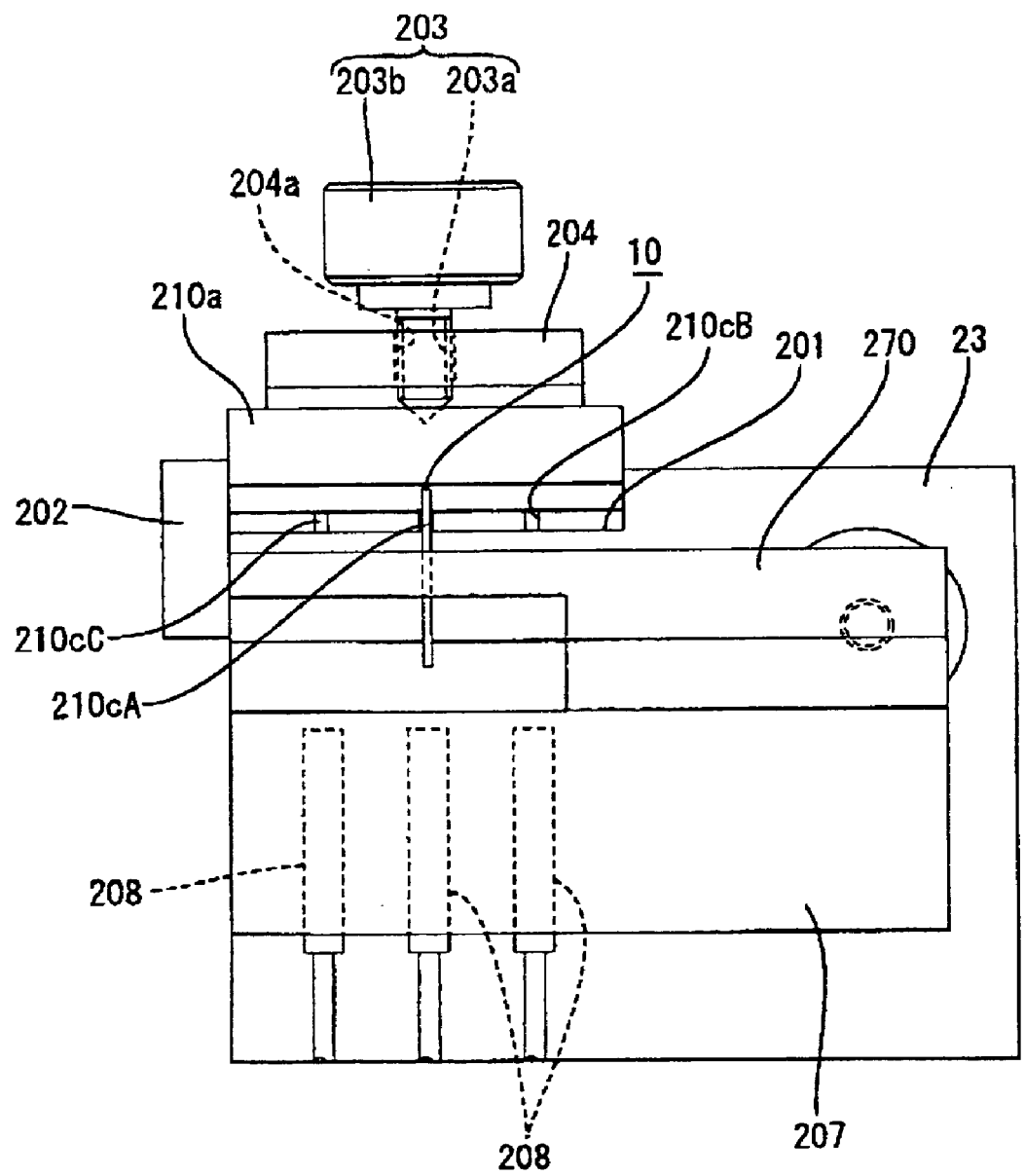
FIG. 17 is a schematic front view of the side of the fixing portion.

As shown in FIGS. 15 to 17, a jig mounting step or projection 201 for mounting the fixed jig 210a is formed at the lateral (upper) end of the fixing portion 23, wherein the other (bottom and rear) surfaces thereof can be brought substantially into contact with the corresponding outer surfaces of the fixed jig 210a. A positioning portion 202 for positioning the fixed jig 210a with respect to widthwise direction (or a direction substantially normal to the moving direction of the jigs 210) is fixed at the upper side of the fixed jig 210a shown in FIG. 15 by being brought substantially into contact with a side surface of the fixed jig 210a. A supporting portion 204 formed with an insertion hole or recess 204a through or into which a jig locking member 203 for locking the fixed jig 210a is at least partly insertable is fixed at the upper end of the jig mounting step 201. A locking recess 210e engageable with the jig locking member 203 is provided on the lateral (upper) surface of the fixed jig 210a. The jig locking member 203 is comprised of a fixed element 203a fixed by being at least partly inserted into the insertion hole 204a of the supporting portion 204 from above, and a movable element 203b engaging or penetrating the fixed element 203a and relatively displaceable with respect to the fixed element 203a. The movable element 203b is substantially vertically movable between a retracted position (not shown) where the leading end thereof is retracted from the locking recess 210e to permit the attachment and detachment of the fixed jig 210a and a locking position where the leading end thereof at least partly enters the locking recess 210e to hold the fixed jig 210a. The movable element 203b is constantly resiliently biased toward the locking position by an unillustrated biasing member and can have (preferably substantially vertical) movements thereof restricted by an unillustrated holding mechanism, wherein such a held state can be canceled preferably by rotating or pivoting the movable element 203b with respect to the fixed element 203a (e.g. similar to a bayonet lock). Accordingly, an operation of mounting and detaching the fixed jig 210a can be easily carried out through one-touch operation of pulling the movable element 203b of the jig locking member 203 while rotating it. The movable jig 210b is also provided with a locking recess 210e similar to the one of the fixed jig 210a, and the slide table 24 is also provided with a jig locking member 203 similar to the one of the fixing portion 23.

Figure 18A:
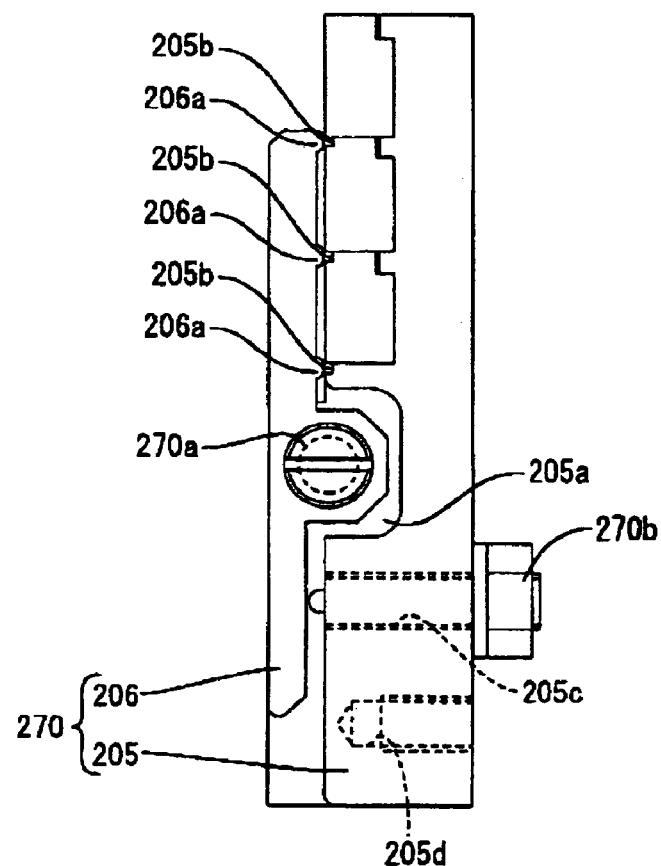
FIGS. 18(A) and 18(B) are a plan view and a front view of a terminal holding portion.
Figure 18B:
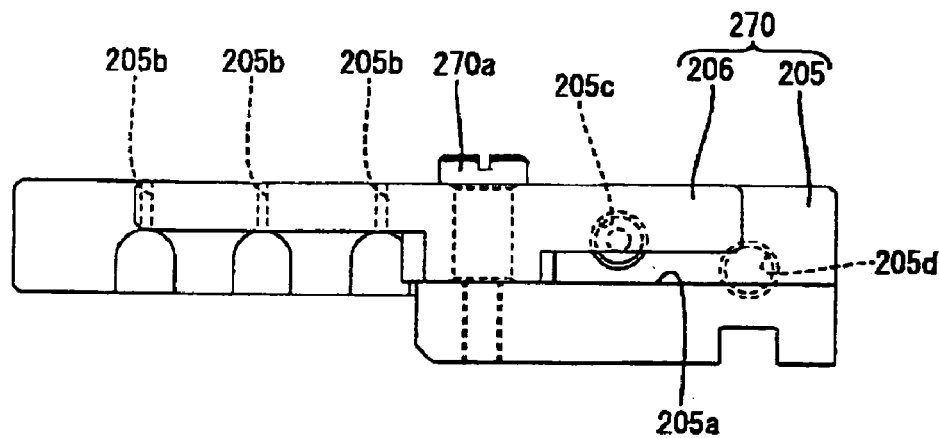

As shown in FIGS. 18(A) and 18(B), a terminal holding portion 270 is provided with a receiving portion 205 and a pushing member 206 for pushing or urging the press-in portion 11 against the receiving portion 205. A mounting step 205a on which the pushing member 206 is mountable from above is formed at the lateral (left) end of the receiving member 205 shown in FIG. 18(A), and a mounting screw 270a for holding the pushing member 206 is screwed down into or engaged with the mounting step 205a from above. A plurality of (e.g. three) terminal mounting grooves 205b for at least partly accommodating a lower part (holdable portion) of the press-in portion 11 of the press-fit terminal 10 are formed preferably substantially side by side at a lateral (upper) side of a surface of the receiving portion 205 substantially facing the pushing member 206. On the other hand, a plurality of (e.g. three) terminal pushing portions 206a projecting toward the corresponding terminal mounting grooves 205b and adapted to push the holdable portion of the press-fit terminal 10 are formed substantially side by side in a surface of the pushing member 206 substantially facing the respective terminal mounting grooves 205b. The positions of the respective terminal mounting grooves 205b and the respective terminal pushing portions 206a (mount position of the press-fit terminal 10) are set such that the press-in portion 11 of the held press-fit terminal 10 substantially conform to the corresponding recess 210cA to 210cC of the jigs 210 with the terminal holding portion 270 properly mounted on the testing unit 200 as shown in FIG. 17. Accordingly, the terminal mounting groove 205b and the terminal pushing portion 206a at an intermediate portion (preferably substantially at a middle portion) substantially correspond to the standard-diameter recesses 210cA, those at the lateral (upper) side in FIG. 18(A) (right side in FIG. 17) substantially correspond to the large-diameter recesses 210cB, and those at the opposite lateral (lower) side in FIG. 18(A) substantially correspond to the small-diameter recesses 210cC.

A screw hole 205c into which a holding-force adjusting screw 270b is at least partly mountable from a side substantially opposite from the pushing member 206 is formed at a part of the side surface of the receiving member 205 below the mounting screw 270a in FIG. 18(A). A leading end portion of the holding-force adjusting screw 270b can come substantially into contact with a part of the side surface of the pushing member 206 at a side substantially opposite from the respective terminal pushing portions 206a with respect to the mounting screw 270a. As the adjusting screw 270b is so screwed as to come closer to or away from the pushing member 206, the pushing member 206 undergoes a seesaw-like displacement about the mounting screw 270a, with the result that the respective terminal pushing portions 206a are displaced substantially toward or away from the corresponding terminal mounting grooves 205b to increase or decrease the holding forces for holding the press-fit terminals 10. A part of the receiving member 205 having the side surfaces of the respective terminal mounting grooves 205b is detachable so as to be exchangeable to the one suitable for the width of the holdable portion of the press-fit terminal 10 to be mounted.

As shown in FIG. 15 or 16, the terminal holding portion 270 is mounted on a movable portion 207 relatively displaceable along the moving directions of the movable jig 210b relative or with respect to the fixing portion 23 by means of an unillustrated self-aligning mechanism (spring plunger, bearing, etc.). Accordingly, the terminal holding portion 270 and the press-fit terminal 10 are free to displace along their displacing directions as the movable jig 210b moves. A plurality of (e.g. three) sensors 208 for detecting in which terminal mounting groove 205b the press-fit terminal 10 at least partly mounted in the terminal holding portion 270 is at least partly mounted (to which recess 210cA to 210cC the mounted position of the press-fit terminal 10 corresponds) are provide substantially side by side in the movable portion 207 below the terminal holding portion 270. Each sensor preferably is a so-called reflection type optical sensor having a light emitting element and a light receiving element located at the same position, wherein the light emitting element and the light receiving element are so mounted as to face upward (align light emitting/receiving directions with the longitudinal direction LD of the press-fit terminal 10). Thus, the presence or absence of the press-fit terminal 10 can be detected regardless of the length of the press-fit terminal 10.

The terminal holding portion 270 is detachable from the movable portion 207. A locking recess 205d engageable with a locking member 209 provided in the movable portion 207 for holding the terminal is provided in a side surface of the receiving portion 205 substantially opposite from the pushing member 206. This locking member 209 has substantially the same construction as the aforementioned jig locking member 203 and includes a fixed element 209a and a movable element 209b. The terminal holding portion 270 can be easily detached through one-touch operation of the movable element 209b. No detailed description is given on the locking member 209 since it is substantially identical to the jig locking member 203.

Figure 19:
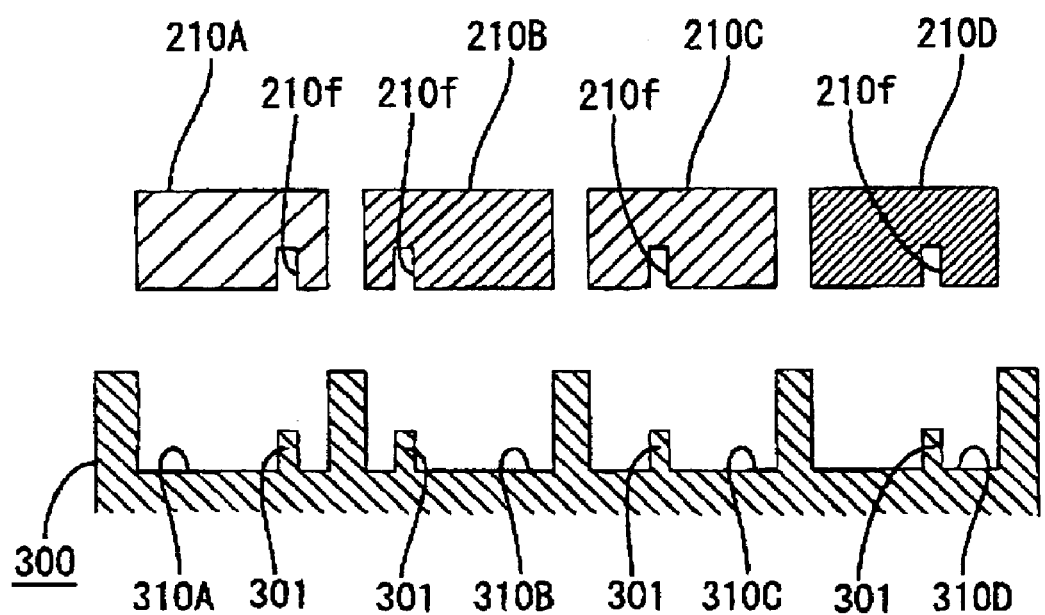
FIG. 19 is a schematic section showing a jig accommodating box and the jig.

As shown in FIG. 12, a plurality of (e.g. four) accommodating chambers 310A to 310D for at least partly accommodating the respective jigs 210A to 210D with the fixed jigs 210a and movable jigs 210b substantially faced each other are provided substantially side by side along longitudinal direction in the jig accommodating box 300. As shown in FIG. 19, identification projections 301 are provided on the bottom surfaces of the respective accommodating chambers 310A to 310D, the positions of the identification projections 301 being different in the respective accommodating chambers 310A to 310D, and identification recesses 210f are formed in (preferably the lower surfaces of) the respective jigs 210A to 210D at such positions as to receive or correspond to the identification projections 301 of the corresponding accommodating chambers 310A to 310D. It should be noted that a pair of identification recesses 210f and a pair of identification projections 301 are so provided as to correspond to the fixed jig 210a and the movable jig 210b of each pair of jigs 210A to 210D (only one identification recess 210f and only one identification projection 301 are shown in FIG. 19). Accordingly, if the jigs 210A to 210D substantially conform to the accommodating chambers 310A to 310D, they can be properly accommodated by at least partly fitting or inserting the identification projections 301 into the identification recesses 210f. If the jigs 210A to 210D do not conform to the accommodating chambers 310A to 310D, the identification projections 301 and the identification recesses 210f are substantially not aligned, wherefore the jigs 210A to 210D are pushed up by the identification projections 301 and cannot be properly accommodated. Thus, that the jigs 210A to 210D do not conform to the accommodating chambers 310A to 310D can be detected. One or more switches 32 similar to those of the first embodiment are provided in the respective accommodating chambers 310A to 310D. More specifically, preferably two switches 32, one for the fixed jig 210a and the other for the movable jig 210b are provided in each of the accommodating chambers 310A to 310D.

Figure 20:
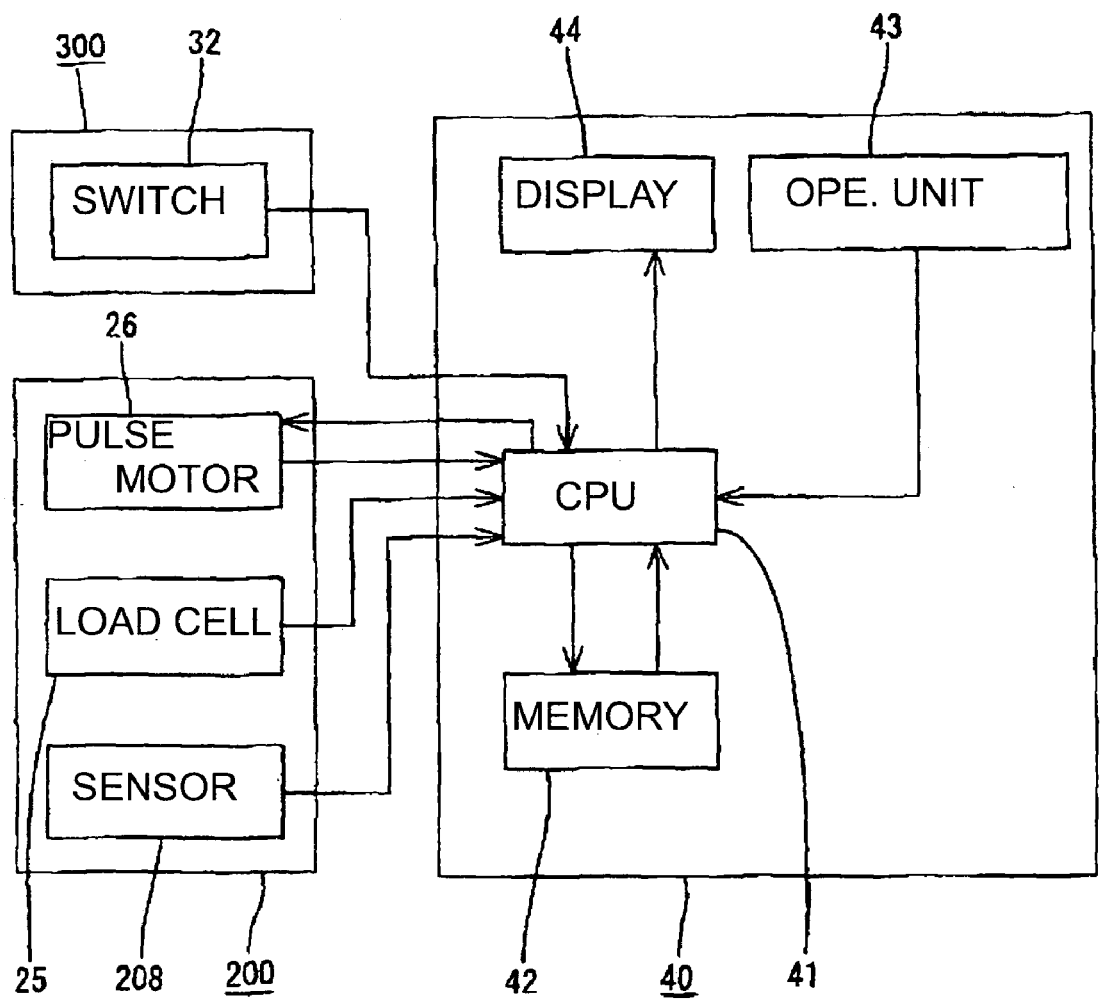
FIG. 20 is a block diagram showing a relationship of a control unit, the testing unit and the jig accommodating box.

A control unit 40 is, as shown in FIG. 20, comprised of a CPU 41, a memory 42, an operation unit 43 and an output device such as a display 44 similar to the first embodiment. Signals from a load cell 25 and a sensor 208 of the testing unit 200 and those from the switches 32 of the jig accommodating box 300 can be inputted to the CPU 41. Further, signals can be transmitted between the CPU 41, a pulse motor 26 and the memory 42. Reference values of the respective judgment reference ranges and data tables for circuit board to be described later are saved in the memory 42. There are preferably three data tables for circuit board: a standard-diameter data table, a large-diameter data table and a small-diameter data table, for each kind of the jigs 210, i.e. each kind of the specification of the circuit board K. In other words, a total of preferably twelve data tables for circuit board are prepared.

Figure 21:
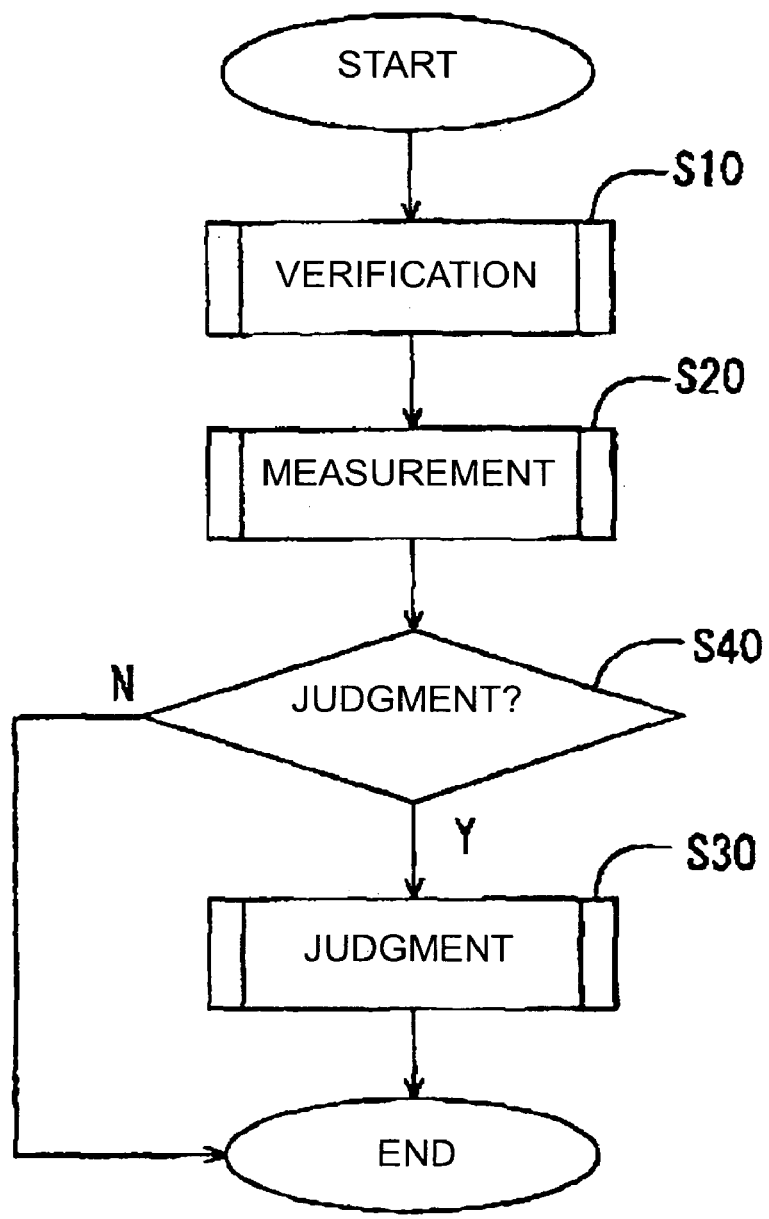
FIG. 21 is a flow chart showing the control of a CPU.

As the control of the CPU 41, the following operations are successively carried out. Specifically, as shown in FIG. 21, a verification process is carried out to verify whether or not the jigs 210 taken out of the jig accommodating box 300 and the mount position of the press-fit terminal 10 in the terminal holding portion 270 substantially conform to initial conditions inputted in a file in advance by means of the operation unit 43 (Step S10); a measurement or detection process conforming to the initial conditions is carried out (Step S20) and a judgment process conforming to the initial conditions is carried out (Step S30). Here, the initial conditions are comprised of one or more (preferably four) specific items: the kind of the jigs 210, a target value dp of the hole diameter of the substitution hole 280A to 280C during the measurement, a measuring method and/or a judging method to be described in detail below. In the case of selecting "no judgment" in the judging method of the initial condition, the operation is ended without carrying out any judgment process after the measurement process (Step S40). The file in which the initial conditions are inputted is saved in the memory 42.

Since there are preferably four kinds of jigs 210 as described above, one kind of them is selected. Then, out of the data tables for circuit board saved in the memory 42, preferably three data tables (standard-diameter data table, large-diameter data table and small-diameter data table) corresponding to the selected jigs 210 are related to the file.

As to the target value dp of the hole diameter, one is selected from the following five values: standard value d0 of the hole diameter; maximum value dmax of a tolerance range of the hole diameter; minimum value dmin of this tolerance range; maximum value dmax and minimum value dmin (two measurements); and standard value d0 of the hole diameter, maximum value dmax and minimum value dmin (three measurements). In the case of selecting the maximum value dmax and the minimum value dmin, the maximum value dmax is first measured in the respective operations below. In the case of selecting the standard value d0 of the hole diameter, the maximum value dmax and the minimum value dmin, measurements are made for the maximum value dmax, the standard value d0 of the hole diameter and the minimum value dmin in this order. These orders of the measurements can be arbitrarily changed.

There are three measuring methods: a designated displacement/designated load measurement (method similar to the first embodiment) according to which the movable jig 210b is displaced away from the fixed jig 210a at a timing when the movable jig 210b reaches the target position or a load F reaches an assumed upper limit value Flim; a point of coincidence measurement according to which the movable jig 210b is displaced away from the fixed jig 210a at a timing when the load F and the hole diameter d in the data table for terminal and the load Fk and the hole diameter dk in the data table for circuit board coincide; and a round trip or recursive measurement according to which an operation of moving the movable jig 210b toward and away from the fixed jig 210a is carried out three times. Any one of these three measuring methods is selected. In the case of selecting the round trip measurement, "no judgment" in the next judging method is automatically selected. Further, the number of round trips in the round trip measurement can be arbitrarily set to two, four or more.

There are four judging methods: a drag/deformation judgment (method similar to the first embodiment) according to which judgment is made based on whether or not the load F at the point of coincidence of the two data tables lies within the judgment reference range and whether or not the load F in the data table for terminal is constantly increasing as the hole diameter d decreases; a resiliently restored amount judgment according to which the load F upon moving the movable jig 210b away from the fixed jig 210a is measured or detected to judge whether or not a displacement amount m of the movable jig 210b until this load F reaches the neighborhood of 0 (F1) lies within a judgment reference range; a method using a combination of the drag/deformation judgment and the resiliently restored amount judgment, and a method making no judgment. Any one of these four methods is or may be selected. In the case of selecting the drag/deformation judgment (including the case combined with the resiliently restored amount judgment), either the "maximum value dmax and minimum value dmin" or the "standard value d0 of the hole diameter, maximum value dmax and minimum value dmin" is selected as the target value dp of the hole diameter. In the case of making no judgment, the board characteristic graphs KG based on the data table for circuit board related by selecting the kind of the jigs 210 can be outputted (preferably displayed on the display 44) preferably together with the terminal characteristic graphs TG based on the measured data table for terminal.

When the aforementioned target value dp of the hole diameter, measuring method and judging method are selected, one or two of the three data tables for circuit board corresponding to the selected jigs 210 are related to the file, and the related data table(s) are used in the measurement process and the judgment process later. More specifically, in the case of selecting the drag/deformation judgment as the judging method, the standard value d0 of the hole diameter and the maximum value dmax are related to the large-diameter data table and the minimum value dmin is related to the small-diameter data table. In the case of selecting the resiliently restored amount judgment or the round trip measurement as the judging method, the standard value d0 of the hole diameter is related to the standard-diameter data table, the maximum value dmax to the large-diameter data table, and the minimum value dmin to the small-diameter data table. In the case of using a combination of the drag/deformation judgment and the resiliently restored amount judgment, the standard value d0 of the hole diameter is related to both the large-diameter data table and the standard-diameter data table.

Figure 23:
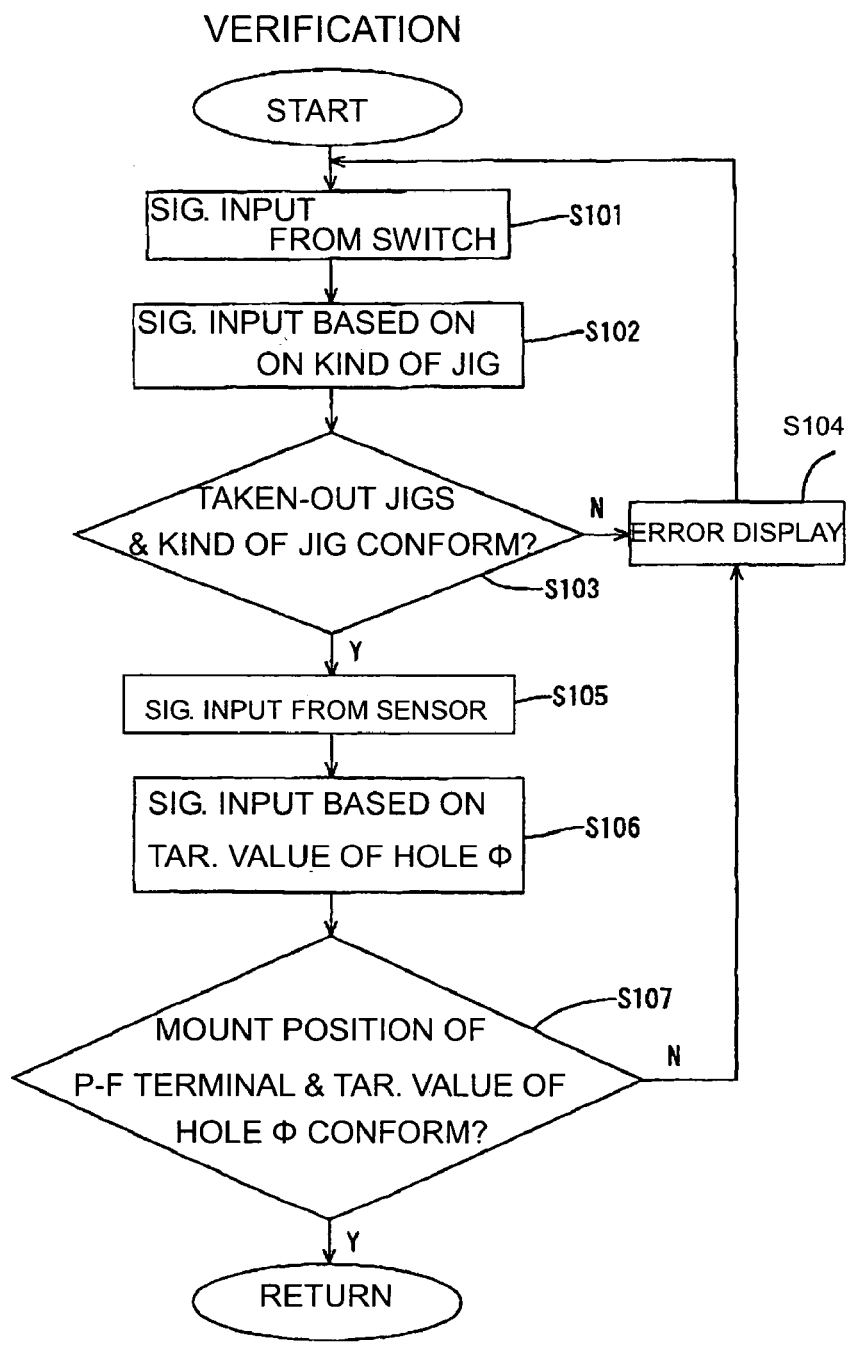
FIG. 23 is a flow chart showing a verification process.

As shown in FIG. 23, when the jigs 210 (fixed jig 210a and movable jig 210b) are taken out of the specified accommodating chamber 310A to 310D of the jig accommodating chamber 300, signals are inputted from the switches 32 corresponding to these jigs 210 to the CPU 41(Step S101). Specifically, the signals are inputted from the switch 32 for the fixed jig 210a and the one for the movable jig 210b to the CPU 41. On the other hand, a signal based on the kind of the jigs 210 set as the initial condition is inputted to the CPU 41 (Step S102). The CPU 41 verifies whether both input signals conform (Step S103). If they do not conform (if the taken-out jigs 210 and the initial condition do not conform or if only one of the fixed jig 210a and the movable jig 210b is taken out), an error output such as an error display is made preferably on the display 44 (Step S104). On the other hand, when the terminal holding portion 270 is mounted on the testing unit 200 after the press-fit terminal 10 is held in the terminal holding portion 270 outside the testing unit 200, a signal is inputted to the CPU 41 from the sensor 208 corresponding to the mount position of the press-fit terminal 10 (Step S105). On the other hand, a signal based on the target value dp of the hole diameter set as the initial condition is inputted to the CPU 41 (Step S106). The CPU 41 verifies whether or not these two signals conform (Step S107). If the signals do not conform, an error output such as an error display (e.g. message "mount position of press-fit terminal is wrong") is made preferably on the display 44 to urge an operator to redo (Step S104). The succeeding measurement process follows if every verification result was positive.

Upon verifying the mount position of the press-fit terminal 10 and the target value dp of the hole diameter (Step S107), the first measurement is based on the maximum value dmax and the second measurement is based on the minimum value dmin if the maximum value dmax and the minimum value dmin are set as the target value dp of the hole diameter as the initial condition; the first measurement is based on the maximum value dmax, the second measurement is based on the standard value d0 of the hole diameter, and the third measurement is based on the minimum value dmin if all the values are set as the target value dp. It does not matter which of the verification of the jigs 210 and the verification of the press-fit terminal 10 is carried out first.

Figure 24:
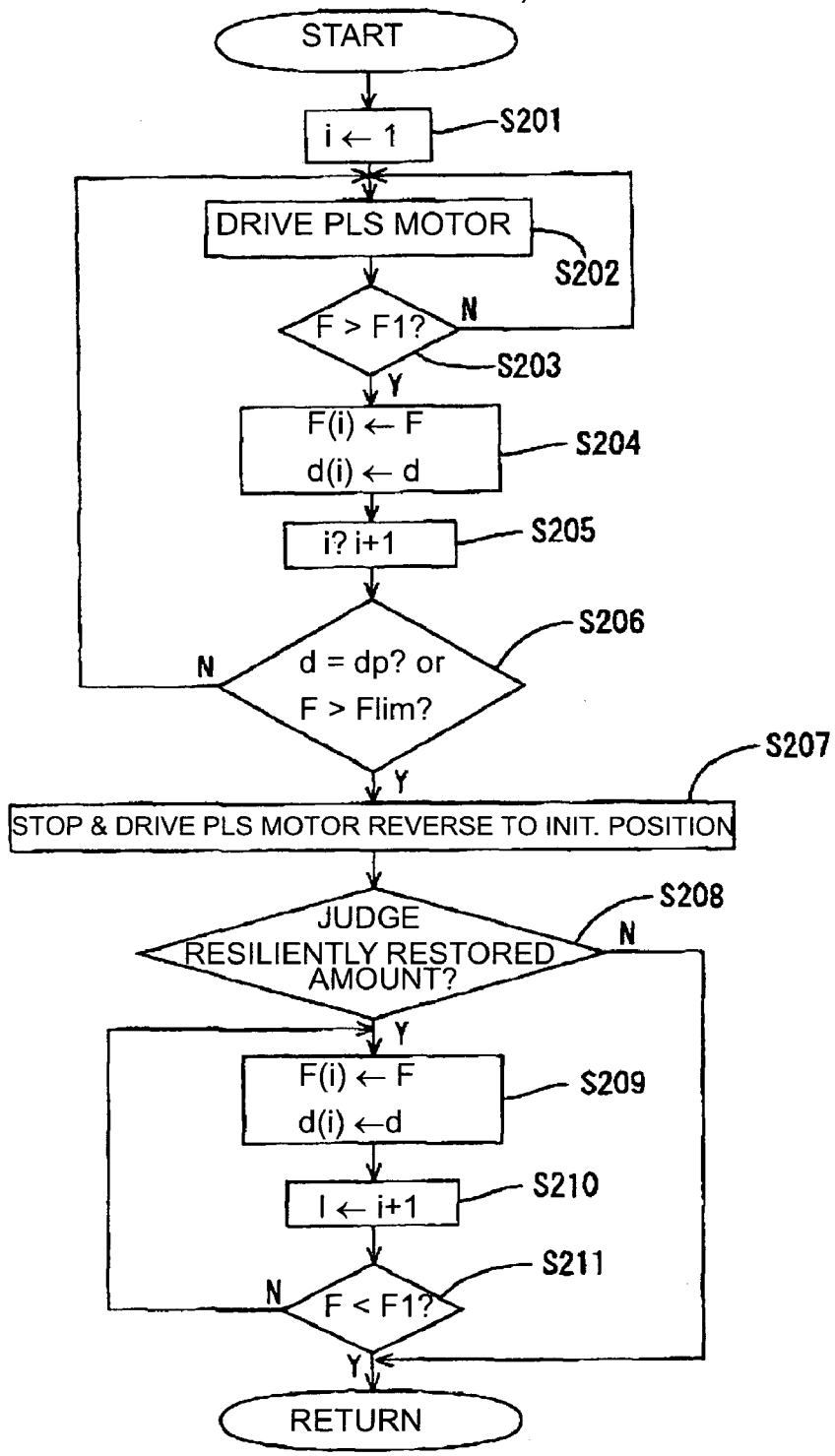
FIG. 24 is a flow chart in the case of carrying out a designated displacement/designated load measurement in a measurement process.
Figure 25:
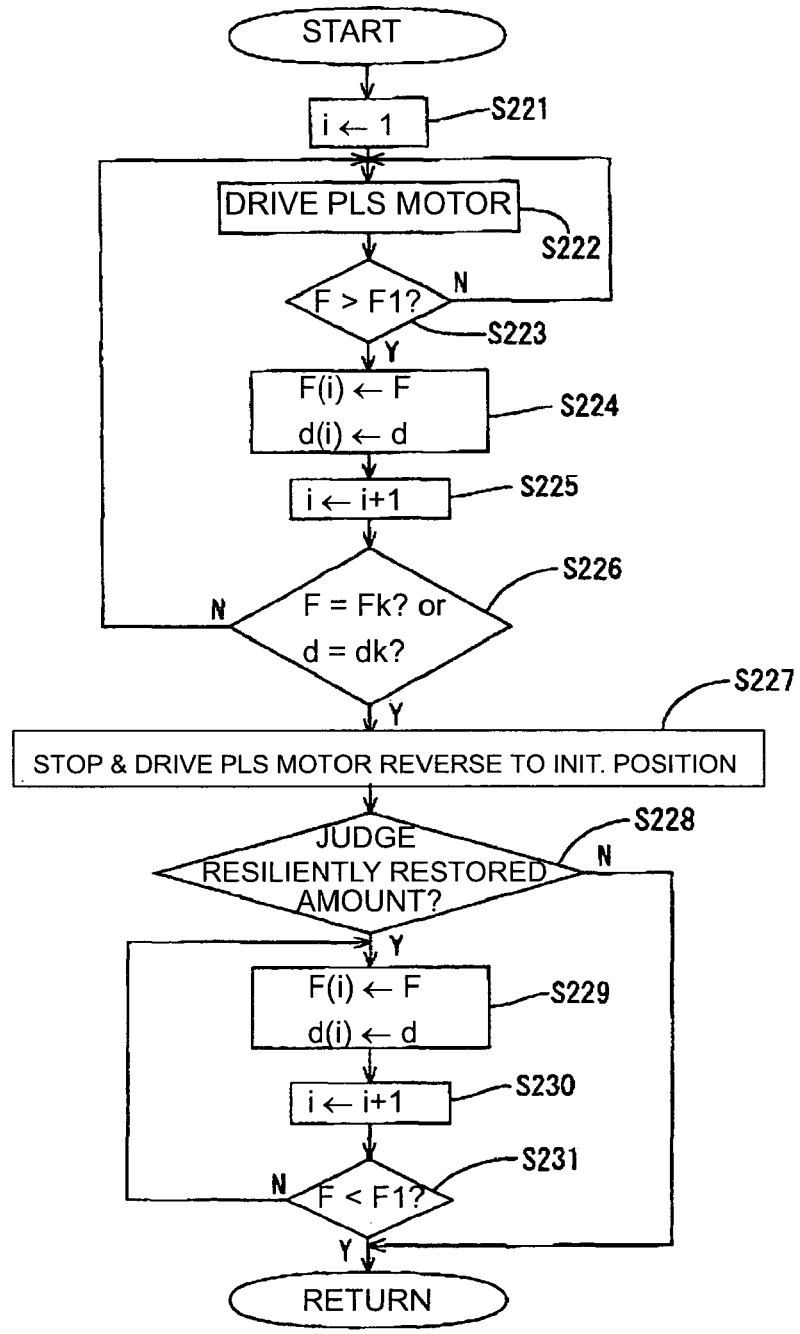
FIG. 25 is a flow chart in the case of carrying out a point of coincidence measurement in the measurement process.
Figure 26:
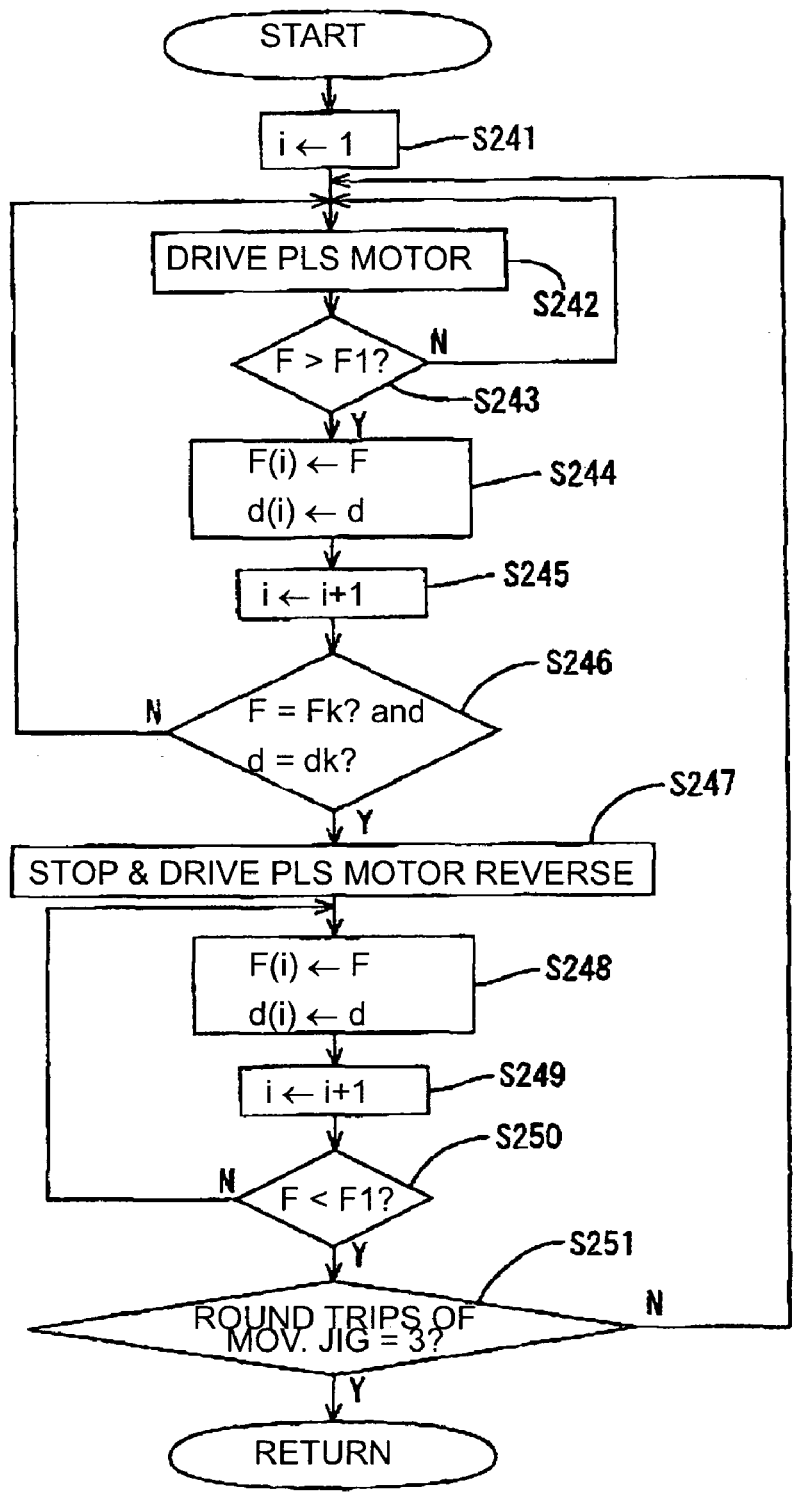
FIG. 26 is a flow chart in the case of carrying out a round trip measurement in the measurement process.

Similar to the first embodiment, as the movable jig 210b is moved toward the fixed jig 210a, the load F and the hole diameter d between the two jigs 210a and 210b being measured or detected are successively written in the data table for terminal (Steps S201 to 205 of FIG. 24, Step S221 to S225 of FIG. 25, Steps S241 to S245 of FIG. 26).

If the designated displacement/designated load measurement was selected as the measuring method as the initial condition, whether or not the hole diameter d has reached the target value dp or the load F has exceeded the assumed upper limit value Flim is judged similar to the first embodiment (Step S206). The measurement continues if neither of the judgment results is positive, whereas the movable jig 210b is returned to an initial position after the pulse motor 26 is temporarily stopped if either of the judgment results is positive (Step S207). Here, whether or not the resiliently restored amount judgment was selected as the judging method as the initial condition is judged (Step S208). If this method was selected, the hole diameter d and the load F in the process of moving the movable jig 210b away from the fixed jig 210a are written in the data table for terminal (Steps S209, S210), and this writing is continued until the load F substantially reaches 0 (F1) (Step S211). In the measurement process, it is also possible to read the data table for terminal and output, preferably occasionally display the terminal characteristic graphs TG preferably on the display 44.

On the other hand, in the case of selecting the point of coincidence measurement as the measuring method as the initial condition, the hole diameter d and the load F being written in the process of moving the movable jig 210b toward the fixed jig 210a are compared with the hole diameter dk and the load Fk in the data table for circuit board upon occasion (Step S226). The data table for circuit board used here is related to the file by selecting the kind of the jigs 210 and the target value dp of the hole diameter as the initial conditions mentioned above. In the case of using a combination of the drag/deformation judgment and the resiliently restored amount judgment as the initial condition and conducting the measurement using the standard value d0 as the target value dp of the hole diameter, the data table for circuit board used is the standard-diameter data table (see FIG. 30(B)). As a result of comparison, the pulse motor 26 is driven in reverse direction to preferably displace the movable jig 210b toward the initial position or away from the fixed jig 210a when the measured hole diameter d substantially agrees with the hole diameter dk in the data table for circuit board and/or the measured load F substantially agrees with the load Fk in the data table for circuit board (Step S227). Similar to the designated deformation/designated load measurement, in this point of coincidence measurement, whether or not the resiliently restored amount judgment is to be made is judged (Step S228), the hole diameter d and the load F in the process of moving the movable jig 210b away are written in the data table for terminal (Step S229, S230) if the resiliently restored amount judgment is to be made, and this writing is continued until the load F substantially reaches 0 (F1) (Step S231). It is also possible to read the data table for terminal and output, preferably display the terminal characteristic graphs TG on the display 44 upon occasion in the measurement process.

Figure 27A:
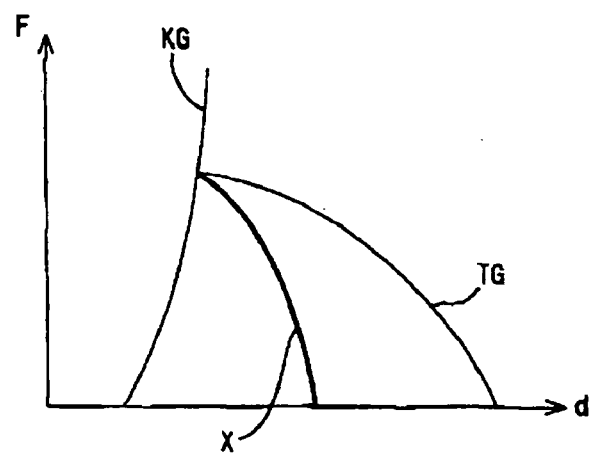
FIG. 27(A) is a graph showing a case where going and returning parts of a terminal characteristic graph overlap each other when the result of the round trip measurement is displayed on the display.
Figure 27B:
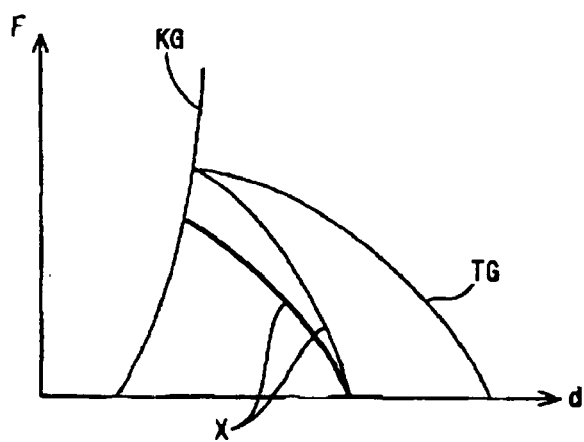
FIG. 27(B) is a graph showing a case where only some of the going and returning parts of the terminal characteristic graph overlap when the result of the round trip measurement is displayed on the display.
Figure 27C:
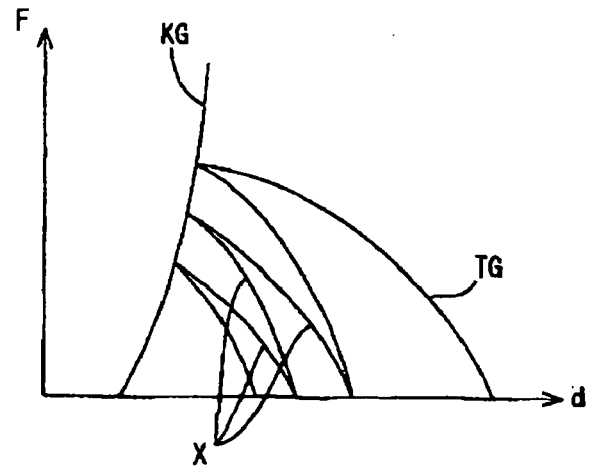
FIG. 27(C) is a graph showing a case where the going and returning parts of the terminal characteristic graph do not overlap at all when the result of the round trip measurement is displayed on the display.

In the case of selecting the round trip measurement as the measuring method as the initial condition, the data table for terminal and the data table for circuit board are compared upon occasion in the measurement process similar to the aforementioned point of coincidence measurement (Step S246) and the pulse motor 26 is driven in reverse direction if the point of coincidence has been reached (Step S247) as shown in FIG. 26. Also in the process of moving the movable jig 210b away from the fixed jig 210a, the hole diameter d and the load F are written in the data table for terminal (Steps S248, S249) until the measured load F substantially reaches 0 (F1) (Step S250). Then, whether or not the number of the round trips of the movable jig 210b has reached three is judged (Step S251) and the measurement is completed if the number has reached three. The data table for terminal is read and the terminal characteristic graphs TG are displayed on the display 44 upon occasion during the measurement process or after the completion of the measurement process. If going and returning parts of the terminal characteristic graph TG overlap each other as shown in FIG. 27(A), the resiliency of the press-in portion 11 is kept although being repeatedly compressed and released. Good durability can be known from this. Conversely, the going and returning parts or paths X of the terminal characteristic graph TG do not overlap each other and the load F decreases as shown in FIGS. 27(B) and 27(C), the press-in portion 11 can be known to have poor durability by undergoing a plastic deformation or the like. More specifically, in the case that only some of the going and returning parts X overlap as shown in FIG. 27(B), it can be thought that a part of the press-in portion 11 undergoes a plastic deformation, but resiliency is kept in the other part even if compression and release are repeated. Further, in the case that the going and returning parts X do not overlap at all as shown in FIG. 27(C), the respective parts of the press-in portion 11 are thought to undergo a plastic deformation every time compression and release are repeated. In the case of selecting this round trip measurement, the operation is completed without carrying out any judgment process as described above (Step S40 shown in FIG. 21).

In the case of selecting the drag/deformation judgment as the judging method as the initial condition, the load Fp at the point of coincidence of the two read data tables is calculated similar to the first embodiment (Steps S31 to S33 of FIG. 10), whether or not the load Fp lies within the judgment reference range is judged (Step S34 of FIG. 10), and whether or not the load F is constantly increasing as the hole diameter d decreases is judged (Step S35 of FIG. 10). The data table for circuit board used here is related to the file by selecting the kind of the jigs 210 and the target value dp of the hole diameter as the aforementioned initial conditions.

Figure 28A:
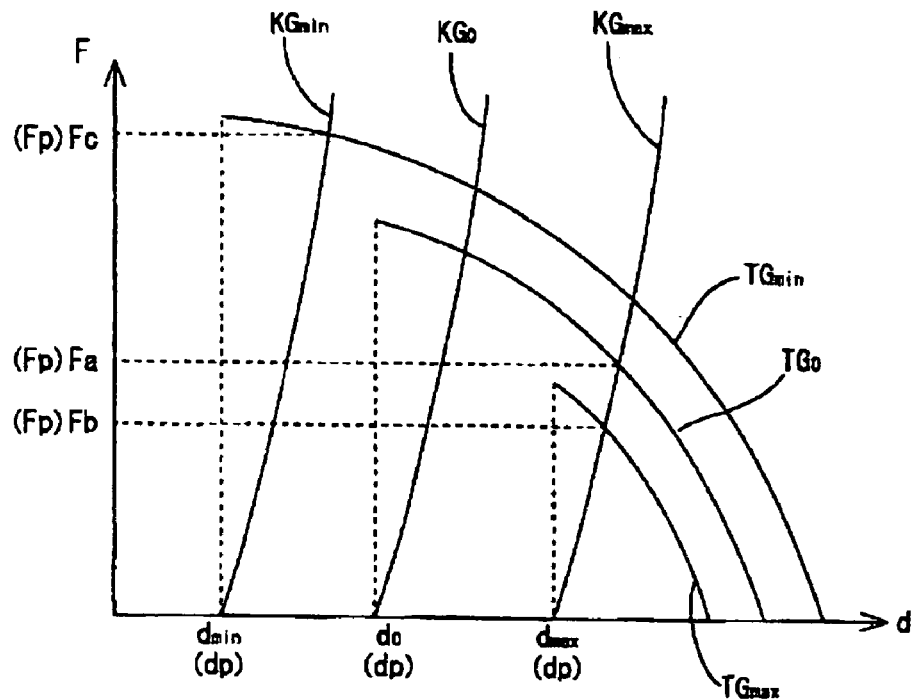
FIG. 28(A) is a graph showing a case where the result of the designated displacement/designated load measurement is displayed on the display when a drag/deformation judgment is made.
Figure 28B:
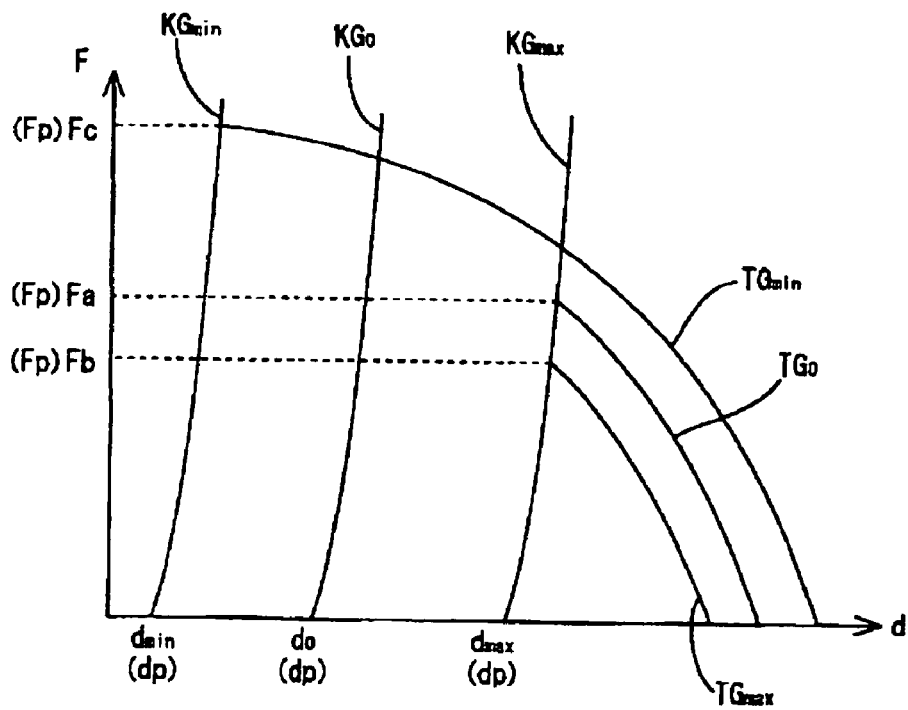
FIG. 28(B) is a graph showing a case where the result of the point of coincidence measurement is displayed on the display when the drag/deformation judgment is made.

Here, the terminal characteristic graphs TG and the board characteristic graph KG displayed on the display 44 in the drag/deformation judgment are described. In the case that the measuring method was the designated deformation/designated load measurement, the load Fp is a load Fa at an intersection with the board characteristic graph KGmax based on the large-diameter data table in the terminal characteristic graph TG0 obtained by setting the standard value d0 of the hole diameter as the target value dp of the hole diameter; a load Fb at an intersection with the board characteristic graph KGmax based on the large-diameter data table in the terminal characteristic graph TGmax obtained by setting the maximum value dmax of the tolerance range as the target value dp of the hole diameter; and a load Fc at an intersection with the board characteristic graph KGmin based on the small-diameter data table in the terminal characteristic graph TGmin obtained by setting the minimum value dmin of the tolerance range as the target value dp of the hole diameter as shown in FIG. 28(A). On the other hand, in the case that the measuring method was the point of coincidence measurement, the load Fp is a load Fa at an intersection with the board characteristic graph KGmax based on the large-diameter data table in the terminal characteristic graph TG0 obtained by setting the standard value d0 of the hole diameter as the target value dp of the hole diameter; a load Fb at an intersection with the board characteristic graph KGmax based on the large-diameter data table in the terminal characteristic graph TGmax obtained by setting the maximum value dmax of the tolerance range as the target value dp of the hole diameter; and a load Fc at an intersection with the board characteristic graph KGmin based on the small-diameter data table in the terminal characteristic graph TGmin obtained by setting the minimum value dmin of the tolerance range as the target value dp of the hole diameter as shown in FIG. 28(B).

Figure 31:
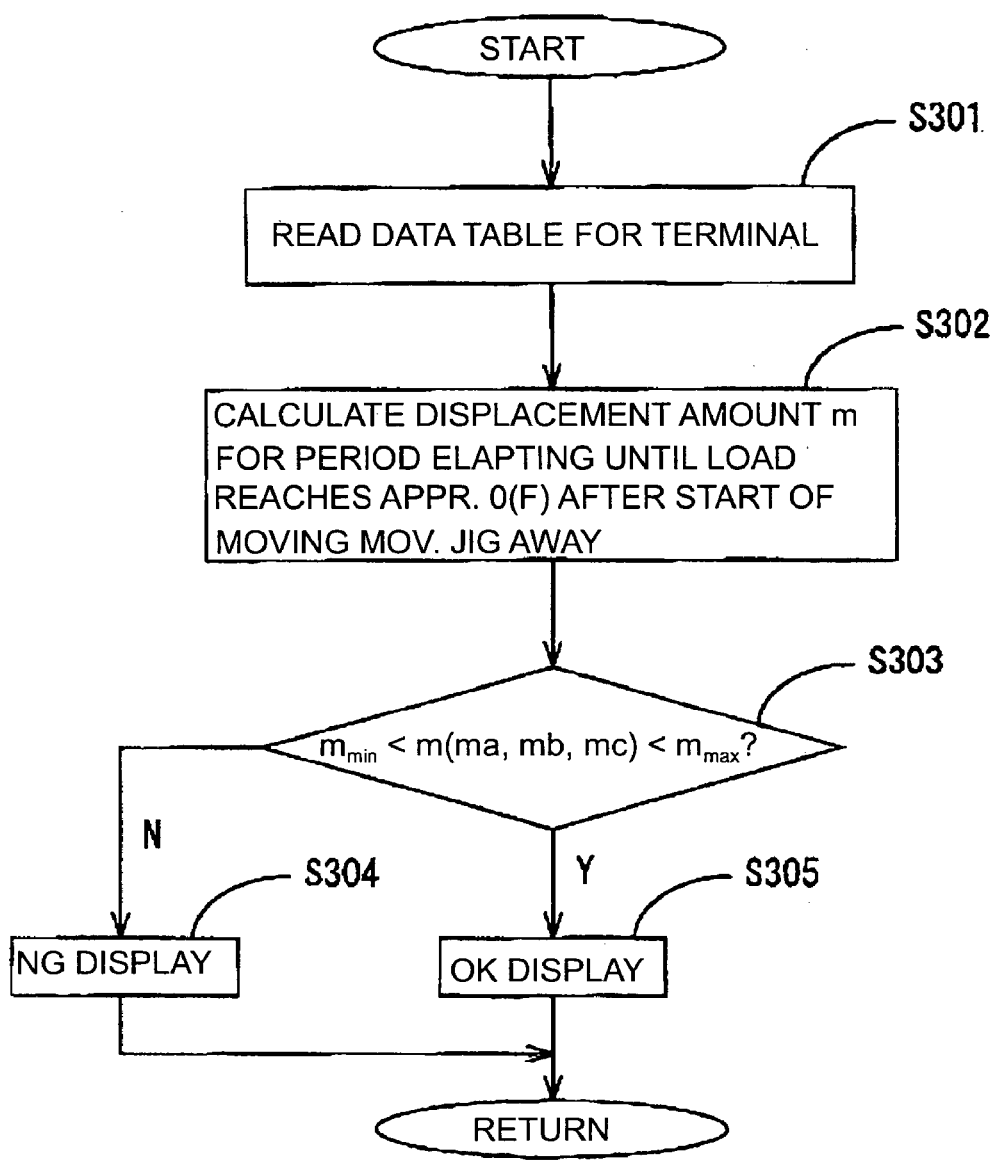
FIG. 31 is a flow chart showing a judgment process.

On the other hand, in the case of selecting the resiliently restored amount judgment as the judging method as the initial condition, the data table for terminal is first read or retrieved as shown in FIG. 31 (Step S301). Then, a displacement amount m (ma when the target value dp of the hole diameter is the standard value d0 of the hole diameter, mb when it is the maximum value dmax of the tolerance range, and mc when it is the minimum value dmin of the tolerance range) of the movable jig 210b until the load F substantially reaches 0 (F1) after the movement of the movable jig 210b away from the fixed jig 210a is started is calculated (Step S302). Thereafter, whether or not this displacement amount m is equal to or above the lower limit value mmin of the judgment reference range saved in the memory 42 and substantially equal to or below the upper limit value mmax is judged (Step S303). An NG display is made on the display 44 (Step S304) if the displacement amount m lies outside the judgment reference range, whereas an OK display is made thereon (Step S305) if the displacement amount m lies within the judgment reference range. Since the displacement amount m of the movable jig 210b at this time corresponds to a restored amount when the press-in portion 11 once squeezed or pressed is resiliently restored, the restored amount of the press-in portion 11 is judged to be excessive if the displacement amount m is substantially above the upper limit value mmax, whereas it is judged that the restored amount of the press-in portion 11 is too little and the press-in portion 11 may be plastically deformed if the displacement amount m is below the lower limit value mmin.

Figure 29A:
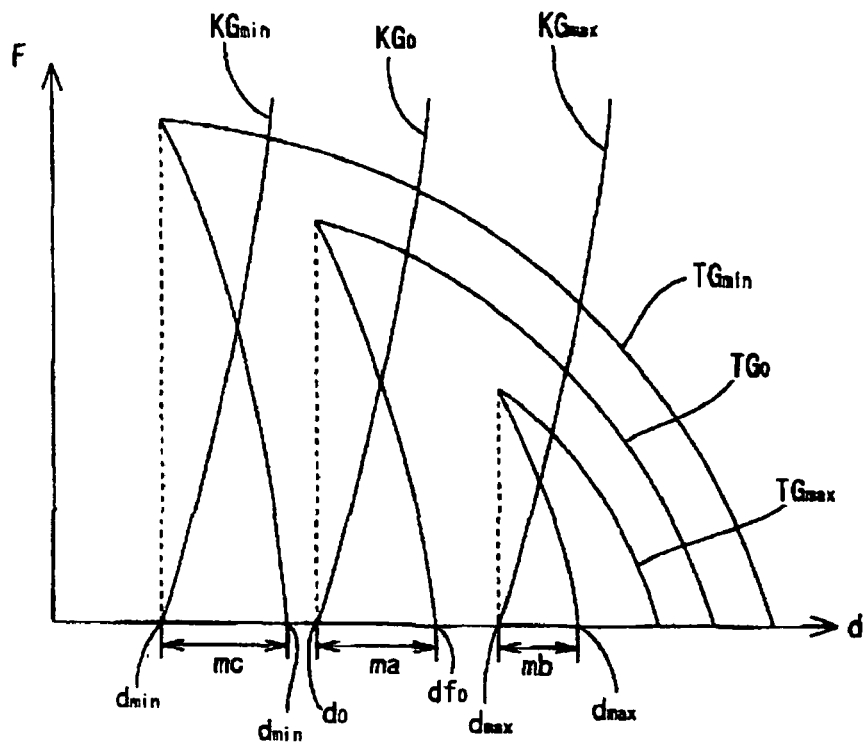
FIG. 29(A) is a graph showing a case where the result of the designated displacement/designated load measurement is displayed on the display when a resiliently restored amount judgment is made.
Figure 29B:
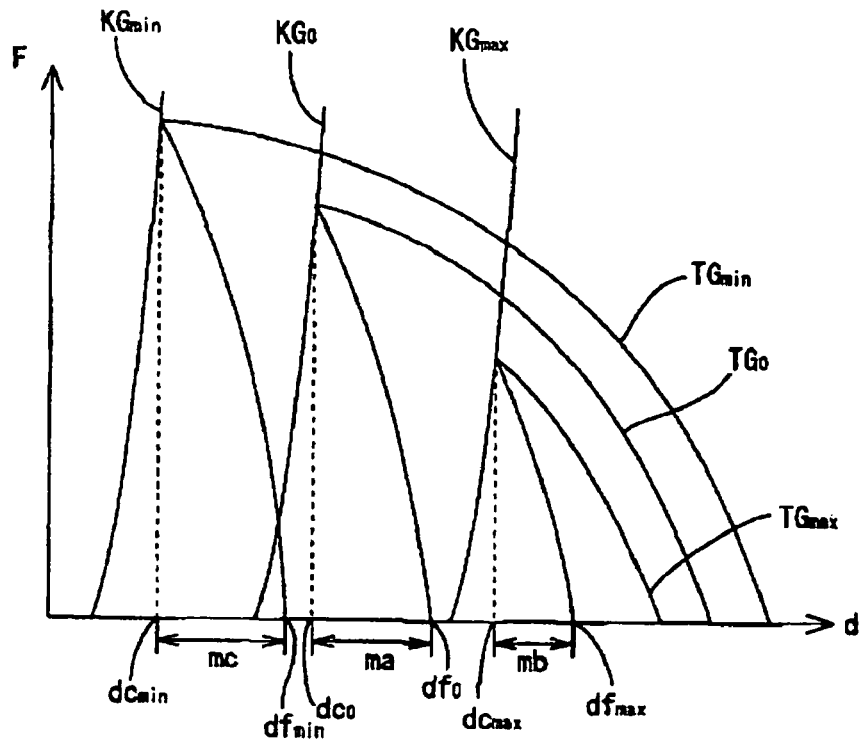
FIG. 29(B) is a graph showing a case where the result of the point of coincidence measurement is displayed on the display when the resiliently restored amount judgment is made.

Here, the terminal characteristic graphs TG and the board characteristic graphs KG outputted (preferably displayed on the display 44) in the resiliently restored amount judgment are described. In the case that the measuring method was the designated displacement/designated load measurement, the displacement amount m is a difference ma between the standard value d0 and a hole diameter df0 when the load substantially becomes 0 in the terminal characteristic graph TG0 obtained by setting the standard value d0 as the target value dp of the hole diameter; a difference mb between the maximum value dmax and a hole diameter dfmax when the load substantially becomes 0 in the terminal characteristic graph TGmax obtained by setting the maximum value dmax of the tolerance range as the target value dp of the hole diameter; and a difference mc between the minimum value dmin and a hole diameter dfmin when the load substantially becomes 0 in the terminal characteristic graph TGmin obtained by setting the minimum value dmin of the tolerance range as the target value dp of the hole diameter as shown in FIG. 29(A). On the other hand, in the case that the measuring method was the point of coincidence measurement, the displacement amount m is a difference ma between a hole diameter dc0 at the intersection with the board characteristic graph KG0 based on the standard-diameter data table and a hole diameter df0 when the load substantially becomes 0 in the terminal characteristic graph TG0 obtained by setting the standard value d0 as the target value dp of the hole diameter; a difference mb between a hole diameter dcmax at the intersection with the board characteristic graph KGmax based on the large-diameter data table and a hole diameter dfmax when the load substantially becomes 0 in the terminal characteristic graph TGmax obtained by setting the maximum value dmax of the tolerance range as the target value dp of the hole diameter; and a difference mc between a hole diameter dcmin at the intersection with the board characteristic graph KGmin based on the small-diameter data table and a hole diameter dfmin when the load substantially becomes 0 in the terminal characteristic graph TGmin obtained by setting the minimum value dmin of the tolerance range as the target value dp of the hole diameter as shown in FIG. 29(B).

Figure 30A:
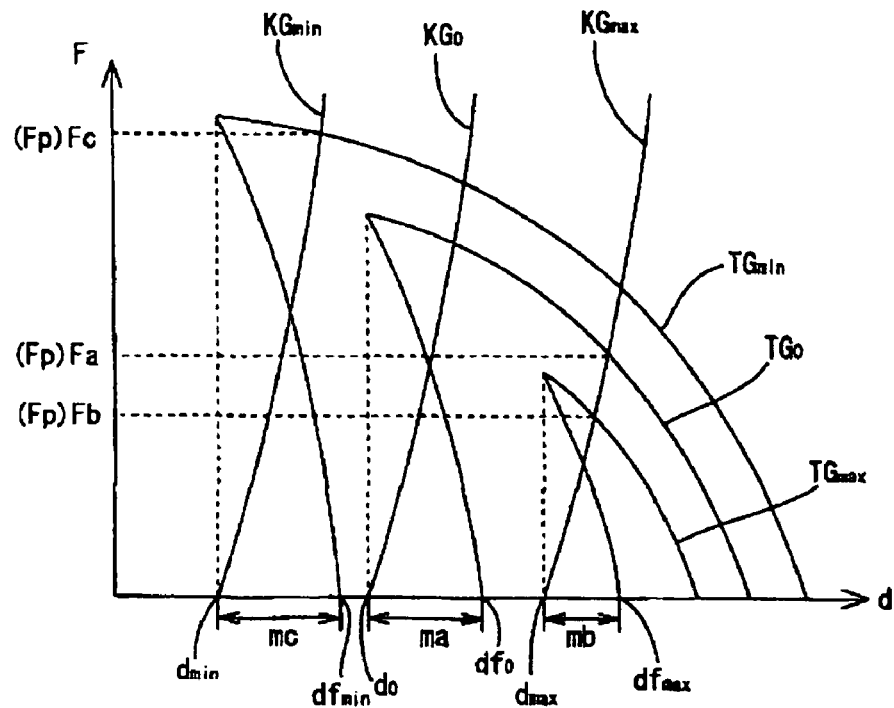
FIG. 30(A) is a graph showing a case where the result of the designated displacement/designated load measurement is displayed on the display when the drag/deformation judgment and the resiliently restored amount judgment are made.
Figure 30B:
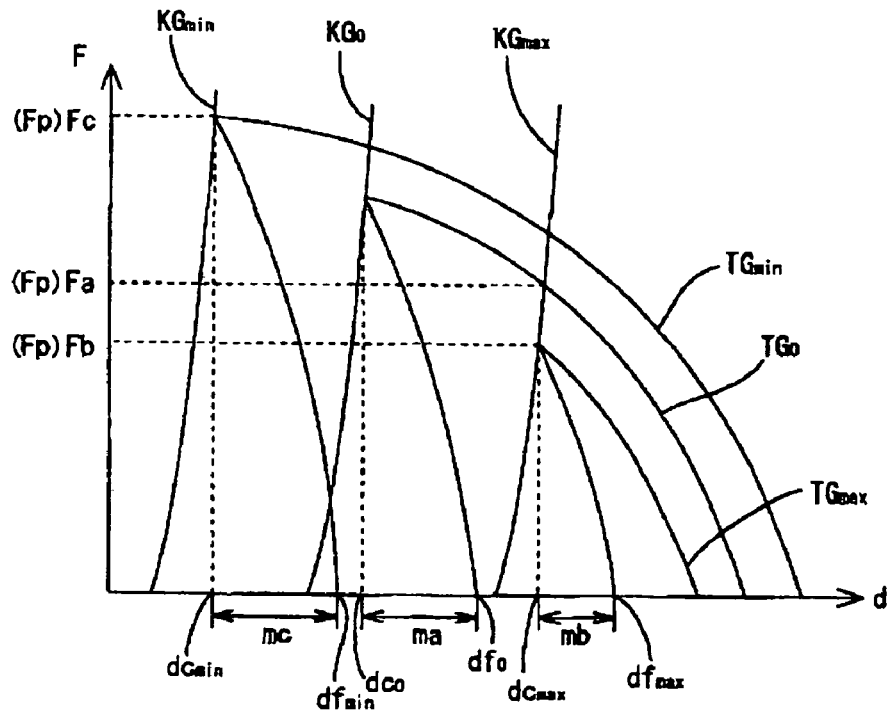
FIG. 30(B) is a graph showing a case where the result of the point of coincidence measurement is displayed on the display when the drag/deformation judgment and the resiliently restored amount judgment are made.

In the case of selecting the combination of the drag/deformation judgment and the resiliently restored amount judgment as the judging method as the initial condition, Step S35 shown in FIG. 10 proceeds to Step S301 shown in FIG. 31, and the OK display is made only for the press-fit terminal 10 judged to be good by both judging methods. Here, the respective graphs and the numerical values are displayed on the display 44 as shown in FIG. 30(A) in the case that the measuring method was the designated displacement/designated load measurement while being displayed on the display 44 as shown in FIG. 30(B) in the case that the measuring method was the point of coincidence measurement. In the case of carrying out the point of coincidence measurement by setting the standard diameter d0 as the target value dp of the hole diameter, the data table for circuit board used in the drag/deformation judgment is the large-diameter data table and the load Fa at the intersection of the terminal characteristic graph TG0 and the board characteristic graph KGmax is judged, whereas the data table for circuit board used in the resiliently restored amount judgment is the standard-diameter data table and the difference ma between the hole diameter dc0 at the intersection of the terminal characteristic graph TG0 and the board characteristic graph KG0 and the hole diameter df0 when the load substantially becomes 0 is judged as shown in FIG. 30(B).

As described above, each jig 210 is integrally provided with the a plurality of (e.g. three) jigs, i.e. the standard-diameter jig 21A, the large-diameter jig 21B and the small-diameter jig 21C shown in the first embodiment, and can form the a plurality of (e.g. three) substitution holes, i.e. the substitution hole 280A corresponding to the standard value d0 of the hole diameter, the substitution hole 280B corresponding to the maximum value dmax of the tolerance range of the hole H, and the substitution hole 280C corresponding to the minimum value dmin of the tolerance range of the hole H when the target position is reached. Thus, operations of, e.g. mounting and detaching the jigs 210 on and from the testing unit 200 can be reduced, thereby improving operability.

Further, a plurality of (e.g. four) kinds of jigs 210A to 210D corresponding to the conditions such as the specification of the circuit board K are provided, and these jigs 210A to 210D are individually at least partly accommodated in the accommodating chambers 310A to 310D of the jig accommodating box 300, wherein the presence and absence of the jigs 210 are detected by the switches 32 provided in the accommodating chambers 310A to 310D. The CPU 41 verifies whether or not the jigs 210 taken out of the accommodating chamber 210A to 210D based on the detection signal conform to the kind of the jigs 210 written in the file as the initial condition by the operator, i.e. data table for circuit board and transfers to the measurement process only when they conform. Thus, a situation where the measurement is made without the taken-out jigs 210 and the initial condition left at variance with each other can be prevented. Further, each jig 210A to 210D is provided with the identification recess 210f, and each accommodating chamber 310A to 310D is preferably provided with the identification projection 301. If the jig 210A to 210D and the accommodating chamber 310A to 310D are a proper combination, the identification projection 301 can be fitted into the identification recess 210f, thereby permitting the jig 210A to 210D to be at least partly accommodated. In the case of a wrong combination, the identification projection 301 cannot be fitted into the identification recess 210f, thereby hindering the erroneous accommodation of the jig 210A to 210D. Thus, a situation where the jigs 210A to 210D are erroneously accommodated into the accommodating chambers 310A to 310D can be prevented.

Further, the press-fit terminal 10 preferably is detected by the sensor 208, and the CPU 41 verifies whether or not the substitution hole 280A to 280C of the jigs 210 corresponding to the mount position of this press-fit terminal 10 conforms to the target value dp of the hole diameter written in the file as the initial condition preferably by the operator, i.e. the data table for circuit board and transfers to the measurement process only when they substantially conform. Thus, a situation where the measurement is started with the press-fit terminal 10 set at the position corresponding to the wrong substitution hole 280A to 280C can be prevented.

In the resiliently restored amount judgment, the hole diameter d and the load F are measured also upon relatively displacing the jigs 210 in a direction substantially away from the press-in portion 11, and the displacement amount m until the load F substantially becomes 0 is calculated. Thus, the resiliently restored amount when the squeezed press-in portion 11 is resiliently restored can be obtained. Further, the CPU 41 judges whether or not the displacement amount m of the jigs 210 lies within the judgment reference range saved in the memory to judge whether or not the press-fit terminal 10 is good, and the judgment result is displayed on the display 44. Thus, the operator needs not judge whether or not the press-fit terminal 10 is good, thereby bettering the operability. Further, in the round trip measurement, the operation of moving the jigs 210 toward and away from the press-in portion 11 is repeated or iterated, and the load F and the hole diameter d between the two jigs 210a and 210b obtained from the displacement amount of the jigs 210 are written in the data table for terminal, and the terminal characteristic graphs TG generated based on this data table for terminal are displayed on the display 44. Thus, it can be judged that the resiliency of the press-in portion 11 is kept if the parts of the terminal characteristic graphs TG corresponding to the movements of the jigs 210 toward and away from the press-in portion 11 overlap. In other words, the durability of the press-in portion 11 can be known.

In the case of carrying out the point of coincidence measurement and the resiliently restored amount measurement, the data table for circuit board and the data table for terminal are compared upon occasion in the measurement process, and the jigs 210 are relatively moved substantially away from each other when these two data tables coincide. Thus, the obtained resiliently restored amount of the press-in portion 11 can be substantially equal to the one obtained when the press-in portion 11 is actually mounted into the hole H of the circuit board K, with the result that a value of the resiliently restored amount approximate to the one obtained at the time of actually mounting can be obtained.

Further, since the press-fit terminal 10 is held by the terminal holding portion 270 and the terminal holding portion 270 is detachably mountable on the movable portion 207 movable as the movable jig 210b is displaced, the terminal holding portion 270 can be removably mounted on or to the testing unit 200 after the press-fit terminal 10 is held in the terminal holding portion 270 outside the testing unit 200. Thus, as compared to a case where the terminal holding portion 270 is fixed to the testing unit 200, the press-fit terminal 10 can be more easily mounted and detached. In addition, since the mounted terminal holding portion 270 can be locked by the locking member 209, which can lock and unlock the terminal holding portion 270 through one-touch operation. Thus, the operability of mounting and detaching the terminal holding portion 270 is good. Further, since the mounted jigs 210 are held by the locking members 203, which can lock and unlock the jigs 210 through one-touch operation, the jigs 210 can be easily mounted and detached, thereby presenting good operability.

The invention is not limited to the above described and illustrated embodiments. For example, the following embodiments are also embraced by the technical scope of the present invention as defined by the claims. Beside the following embodiments, various changes can be made without departing from the scope and spirit of the present invention as defined by the claims.

Although the respective graphs and the like are displayed on the display in addition to the judgment results (OK display, NG display, error display) in the respective foregoing embodiments, only the judgment results may be displayed. Characters to be displayed can be suitably changed, and something other than characters such as figures or symbols may be displayed.

Although the display is shown as a notifying or output means in the foregoing embodiments, lamps having two different colors may be selectively turned on or buzzers having two different sounds or other output means may be selectively driven to notify the judgment result to the operator.

Although only one of the pair of jigs is displaced in the foregoing embodiments, both jigs may be displaced.

Although three kinds of jigs are used in the first embodiment, one, two or four kinds of jigs may be used. Further, the jig accommodating box may be possibly omitted.

Although the press-in portion having a substantially N-shaped cross section is measured in the foregoing embodiments, press-fit terminals formed with press-in portions having various shapes in addition to the N-shaped press-in portion can be measured.

The standard-diameter jigs and the standard-diameter data table as the data table for circuit board are prepared in the first embodiment. They are advantageous in obtaining a drag when the press-fit terminal and the circuit board are produced without having any processing error, but not necessarily required in judging whether or not the press-fit terminal is good. Therefore, they may be dispensed with.

Although whether or not the press-fit terminal is good is judged in the first embodiment, only the load at the point of coincidence of the two data tables may be obtained and no judgment may be made according to the present invention.

The number of the recesses formed in the jigs may be two (large-diameter recess and small-diameter recess), four or more in the second embodiment according to the present invention.

The number of kinds of jigs may be below four or above four in the second embodiment. In such a case, the jig accommodating box can be changed in accordance with the kinds of the jigs, but the jig accommodating box may be externally provided.

In the second embodiment, the jigs may be provided with the identification projections and the accommodating chambers of the jig accommodating box may be provided with the identification recesses. Further, the jigs and the accommodating chambers of the first embodiment may be provided with the identification projections and the identification recesses. Alternatively or additionally other identification means such as transponders and detectors, magnetic, electric and/or optic identification means or other substantially corresponding or conforming shapes (e.g. polygonal shapes) may be provided.

The number, mount positions, postures and kinds of the sensors provided in the movable portion can be arbitrarily changed in the second embodiment. For example, transmission type optical sensors may be used as the sensors, wherein light emitting elements may be provided on the slide table, i.e. on the movable jig, and light receiving elements may be provided on the terminal holding portion or the movable portion, i.e. on the fixed jig. It is, of course, also possible to provide the light emitting elements on the fixed jig and the light receiving elements on the movable jig in such a case.

In the second embodiment, the resiliently restored amount judgment may not be made although the displacement amount until the load substantially becomes 0 after the start of the movement of the jig away from the press-in portion is measured during the measurement and the measurement result is displayed on the display. In other words, only the resiliently restored amount of the press-in portion may be obtained without making any judgment. Further, in the first embodiment, the displacement amount until the load substantially becomes 0 after the start of the movement of the jig away from the press-in portion may be measured. In such a case, judgment may be made as to whether the measured displacement amount lies within the judgment reference range or the measured data may be compared with the data table for circuit board upon occasion and the jigs may be displaced in separating directions when they reach a point of coincidence as in the second embodiment.

In the second embodiment, bolts may be used, for example, as the jig locking members and the locking members for holding the terminal, and the jigs and the terminal holding portion may be locked and unlocked by screwing the bolt to advance or retreat. Further, the jig locking members may be used for the jigs shown in the first embodiment, and the locking members for holding the terminal may be used by making the terminal holding portion shown in the first embodiment detachably mountable on the movable portion.

In the second embodiment, other judgments such as the resiliently restored amount judgment may be made even in the case of making the round trip measurement.

What is claimed is:

1. A measuring apparatus for obtaining a drag acting when a press-in portion (11) of a press-fit terminal (10) is pressed into a hole (H) of an electric device (K) and held by being squeezed and widening the hole (H), comprising:

at least two jigs (21; 210) relatively displaceable to hold the press-in portion (11) from substantially opposite sides along a direction at an angle to a longitudinal direction (LD) of the press-in portion (11) and capable of forming a substitution hole (28; 280) having a dimension substantially corresponding to a hole diameter of the hole (H) when a target position is reached;

displacement measuring means (26) for measuring displacement of the jigs (21; 210);

a load measuring means (25) for measuring a load acting on the jigs (21; 210) from the press-in portion (11) when the jigs (21; 210) are moved closer to the press-in portion (11);

a storage (42) for storing a data table for the electric device (K) written with a load necessary to widen the hole (H) of the electric device (K) and the hole diameter of the widened hole, and a calculating portion (41) for receiving the measured load and the hole diameter between the jigs (21; 210) obtained from the measured displacement amount of the jigs (21; 210) and calculating a load at a point of coincidence of a data table for the terminal and the data table for the electric device (K).

2. The measuring apparatus of claim 1, further comprising:

a judging means (41) for judging if the load at the point of coincidence of the two data tables lies within a judgment reference range saved in the storage (42) to judge whether the press-fit terminal (10) is good, and a notifying means (44) for notifying a judgment result by the judging means to an operator.

3. The measuring apparatus of claim 2, wherein the judging means (41) also judges whether the measured load is constantly increasing as the hole diameter between the two jigs (21; 210) decreases.

4. The measuring apparatus of claim 2, wherein the notifying means (44) comprises a display (44) for displaying the judgment result.

5. The measuring apparatus of claim 4, wherein at least one of a terminal characteristic graph (TG) generated based on the data table for terminal, a board characteristic graph (KG) generated based on the data table for electric device (K) and the judgment reference range are displayed on the display (44).

6. The measuring apparatus of claim 1, wherein:

there are at least two kinds of exchangeable jigs (21; 210) including large-diameter jigs (21B; 210B) capable of forming a substitution hole (28; 280) having a dimension corresponding to a maximum value of a tolerance of the hole diameter of the hole (H) when the target position is reached, and small-diameter jigs (21C; 210C) capable of forming a substitution hole (28; 280) having a dimension corresponding to a minimum value of the tolerance of the hole diameter of the hole (H) when the target position is reached;

there are at least two kinds of data tables for the electric device, including a large-diameter data table obtained by setting the maximum value as the hole diameter at a starting point, and a small-diameter data table obtained by setting the minimum value as the hole diameter at the starting point; and the calculating portion (41) calculates a load at a point of coincidence of the data table for electric device conforming to the selected jigs and the data table for the measured terminal.

7. The measuring apparatus of claim 1, further comprising:

a jig accommodating box (30; 300) provided with accommodating chambers (31; 310) for at least partly accommodating the respective jigs;

a jig detecting means (32) provided in correspondence with the respective jigs (21; 210) for detecting whether the respective jigs (21; 210) are at least partly accommodated in the accommodating chambers (31; 310); and a verifying means (41) for verifying whether the jigs (21; 210) taken out of the jig accommodating box (30; 300) conform to the data table for the electric device selected by an operator in accordance with a detection signal from the jig detecting means (32), wherein the calculating portion (41) starts a measurement process only when a verification result by the verifying means (41) shows conformity.

8. The measuring apparatus of claim 1, wherein a driving source (26) for displacing the jigs (21; 210) comprises a pulse motor (26) and the displacement amount measuring means identifies a pulse number given to the pulse motor (26) and obtains the displacement amount of the jigs (21; 210) from the pulse number.

9. The measuring apparatus of claim 1, wherein an escaping space (29) is defined between the two jigs (21; 210) when the target position is reached.

10. The measuring apparatus of claim 1, wherein the jigs (21; 210) include a fixed jig (21a; 210a) and a movable jig (21b; 210b) relatively displaceable toward and away from the fixed jig (21a; 210a), and the measuring apparatus further comprises a terminal holding portion (27) capable of holding the press-fit terminal (10) and displacing the press-fit terminal (10) as the movable jig (21b; 210b) is displaced.

11. The measuring apparatus of claim 1, wherein each jig (21; 210) is provided integrally with at least a large-diameter jig (21B; 210B) and a small-diameter jig (21C; 210C) so that at least two substitution holes (28; 280) are formed.

12. The measuring apparatus of claim 11, wherein a plurality of kinds of jigs (21A–C; 210A–C) are prepared in correspondence with the specification of the electric device (K), and the measuring apparatus further comprises:

a jig accommodating box (30; 300) with at least one accommodating chamber (31; 310) for accommodating the respective jigs (21; 210), a jig detecting means (32) provided in correspondence with the respective jigs (21; 210) for detecting whether the respective jigs (21; 210) are accommodated in the accommodating chambers (31; 310), and a verifying means (41) for verifying whether the jigs (21; 210) taken out of the jig accommodating box (30; 300) conform to the data table for electric device selected by an operator in accordance with a detection signal from the jig detecting means (32), wherein the calculating portion starts a measurement process only when a verification result by the verifying means (41) shows conformity.

13. The measuring apparatus of claim 12, wherein the jigs (21; 210) and the accommodating chambers (31; 310) comprise identification recess/projection means (210f; 301) which are engageable with each other to permit the accommodation of the jigs (21; 210) in the case of a correct combination of the jigs (21; 210) and the accommodating chamber (31; 310) while being not engageable to prevent the jigs (21; 210) from being properly accommodated in the case of a wrong combination.

14. The measuring apparatus of claim 13, wherein the press-fit terminal (10) is set at a position corresponding to one of the respective substitution holes (28; 280) in the jigs (21; 210), and the measuring apparatus further comprises:

a terminal detecting means (208) for detecting the press-fit terminal (210), and a verifying means (41) for verifying whether the substitution hole (280) corresponding to the set position of the press-fit terminal (10) conforms to the data table for the electric device selected by an operator in accordance with a detection signal from the terminal detecting means (208), wherein the calculating portion (41) starts a measurement process only when a verification result of the verifying means (41) shows conformity.

15. The measuring apparatus of claim 1, wherein:
the jigs (21; 210) are relatively displaced in separating directions after being moved closer to the press-in portion (11) to squeeze the press-in portion (11); and
the displacement amount measuring means (26) measures the displacement amount of the jigs (21; 210) and the load measuring means measures the load also when the jigs (21; 210) are relatively displaced in the separating directions, wherein the displacement amount of the jigs (21; 210) is calculated until the load substantially becomes 0.

16. The measuring apparatus of claim 15, further comprising:
a judging means for judging whether the displacement amount of the jigs (21; 210) lies within a judgment reference area saved in the storage (42) to judge whether the press-fit terminal (10) is good, and
a display (44) for notifying a judgment result by the judging means to an operator.

17. The measuring apparatus of claim 1, wherein:
the jigs (21; 210) are relatively displaced in separating directions after being moved closer to the press-in portion to squeeze the press-in portion (11),
the jigs (21; 210) are repeatedly moved closer to and away from the press-in portion (11),
the load and the hole diameter between the two jigs (21; 210) obtained from the displacement amount during the repeated movements of the jigs (21; 210) are written in the data table for the terminal, and
a terminal characteristic graph (TG) generated based on the data table for terminal is displayed on a display (44).

18. The measuring apparatus of claim 17, wherein the data table for the electric device and the data table for terminal are compared in a measurement process, and the jigs (21; 210) are relatively displaced in separating directions when the data table for the electric device and the data table for the terminal substantially reach a point of coincidence.

19. The measuring apparatus of claim 1, wherein the jigs (21; 210) include a fixed jig (21a; 210a) and a movable jig (21b; 210b) relatively displaceable toward and away from the fixed jig (21a; 210a), and the measuring apparatus preferably further comprises a terminal holding portion (27) capable of holding the press-fit terminal (11) and displacing the press-fit terminal (11) as the movable jig (21b; 210b) is displaced.

20. The measuring apparatus of claim 19, wherein the terminal holding portion (27) is detachably mountable on a movable portion movable as the movable jig (21b; 210b) is displaced, and comprises a locking member for locking the mounted terminal holding means, wherein the locking member can lock and unlock the terminal holding portion through one-touch operation.

21. The measuring apparatus of claim 1, further comprising a jig locking member (203) for holding the jigs (21; 210) in their mounted state, wherein the jig locking member (203) can lock and unlock the jigs (21; 210) through one-touch operation.

22. The measuring apparatus of claim 21, wherein a driving source (26) for displacing the jigs (21; 210) comprises a pulse motor (26) and the displacement amount measuring means measures a pulse number given to the pulse motor (26) and obtains the displacement amount of the jigs (21; 210) from the pulse number.

23. A measuring method for obtaining a drag acting when a press-in portion (11) of a press-fit terminal (10) is pressed into a hole (H) of an electric device (K) to be held by being squeezed and substantially widening the hole (H), comprising the following steps:
relatively displacing at least one pair of jigs (21; 210) to hold the press-in portion (11) from substantially opposite sides along a direction at an angle to the longitudinal direction (LD) of the press-in portion (11), thus forming a substitution hole (28; 280) having a dimension substantially corresponding to a hole diameter of the hole (H) when a target position is reached;
measuring a displacement amount of the jigs (21; 210);
measuring a load acting on the jigs (21; 210) from the press-in portion (11) when the jigs (21; 210) are moved closer to the press-in portion (11);
storing a data table for the electric device written with a load necessary to widen the hole (H) of the electric device (K) and the hole diameter of the widened hole, and
outputting the measured load and the hole diameter between the two jigs (21; 210) obtained from the measured displacement amount of the jigs (21; 210) and calculating a load at a point of coincidence of the data table for the terminal and the data table for the electric device.

24. The measuring method of claim 23, further comprising a step of judging whether the load at the point of coincidence of the two data tables lies within a judgment reference range saved in the storage (42) to judge whether the press-fit terminal (10) is good, and notifying a judgment result by the judging means to an operator.

25. Computer program product comprising computer-readable storage medium which when loaded on a computer performs the measuring method of claim 23.

* * * * *